US012752080B2

(12) United States Patent
Piferi

(10) Patent No.: US 12,752,080 B2
(45) Date of Patent: Oct. 6, 2026

(54) SURGICAL THERAPY SYSTEMS AND RELATED METHODS

(71) Applicant: ClearPoint Neuro, Inc., Solana Beach, CA (US)

(72) Inventor: Peter G. Piferi, Orange, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 845 days.

(21) Appl. No.: 18/175,635

(22) Filed: Feb. 28, 2023

(65) Prior Publication Data

US 2023/0302255 A1 Sep. 28, 2023

Related U.S. Application Data

(60) Provisional application No. 63/322,257, filed on Mar. 22, 2022.

(51) Int. Cl.
*A61M 25/01* (2006.01)
*A61B 90/10* (2016.01)
(Continued)

(52) U.S. Cl.
CPC ............. *A61M 25/01* (2013.01); *A61B 90/10* (2016.02); *A61B 90/11* (2016.02); (Continued)

(58) Field of Classification Search
CPC .......... A61M 25/01; A61M 2025/0681; A61B 90/10; A61B 90/11; A61B 17/3462; A61B 2090/103; A61B 2090/374
See application file for complete search history.

(56) References Cited

U.S. PATENT DOCUMENTS 3,352,306 A 11/1967 Hrisch
3,540,447 A 11/1970 Howe
(Continued)

FOREIGN PATENT DOCUMENTS

CA 2655515 A1 8/2010
DE 19826078 C1 8/1999
(Continued)

OTHER PUBLICATIONS

Chen et al. "Combination Therapy with Irinotecan and Protein Kinase C Inhibitors in Malignant Glioma" Cancer 97(9 Suppl):2363-2373 (2003).

(Continued)

*Primary Examiner* — Tasnim Mehjabin Ahmed
(74) *Attorney, Agent, or Firm* — Myers Bigel, P.A.

(57) ABSTRACT

Systems for treatment include a sheath assembly with a guide sheath and a shoulder, a stylet releasably couplable to the guide sheath and extending a distance out of a distal end thereof for rigidity to facilitate proper positioning, a bolt configured to hold a seal member, a bolt nut coupleable to the bolt member to clamp the sheath assembly and the seal member in the bolt. A therapy device such as a flexible catheter is releasably interchangeably held in the guide sheath in lieu of the stylet. A portion of the flexible catheter can remain in the guide sheath in a brain of a patient with the guide sheath held by the bolt and bolt nut with another external portion residing outside these devices to allow the portion of the flexible catheter to move with the brain of the patient during treatment.

22 Claims, 27 Drawing Sheets

(51) Int. Cl.

| | |
|---|---|
| ***A61B 90/11*** | (2016.01) |
| *A61B 17/34* | (2006.01) |
| *A61B 90/00* | (2016.01) |
| *A61M 25/06* | (2006.01) |

(52) U.S. Cl.
CPC ..... *A61B 17/3462* (2013.01); *A61B 2090/103* (2016.02); *A61B 2090/374* (2016.02); *A61M 2025/0681* (2013.01)

(56) References Cited

U.S. PATENT DOCUMENTS 3,824,157 A 7/1974 Macur
3,856,009 A 12/1974 Winnie
4,149,535 A 4/1979 Volder
4,239,042 A 12/1980 Asai
4,265,928 A 5/1981 Braun
4,327,722 A 5/1982 Groshong et al.
4,449,532 A 5/1984 Storz
4,531,943 A 7/1985 Van Tassel et al.
4,543,091 A 9/1985 Froning et al.
4,543,092 A 9/1985 Mehler et al.
4,545,390 A 10/1985 Leary
4,597,421 A 7/1986 Wells
4,623,789 A 11/1986 Keda et al.
4,629,450 A 12/1986 Suzuki et al.
4,646,752 A 3/1987 Swann et al.
4,705,511 A 11/1987 Kocak
4,738,658 A 4/1988 Magro et al.
4,739,768 A 4/1988 Engelson et al.
4,781,691 A 11/1988 Gross
4,820,349 A 4/1989 Saab
4,846,799 A 7/1989 Tanaka et al.
4,897,077 A 1/1990 Cicciu et al.
4,903,707 A * 2/1990 Knute ................ A61B 17/3403 600/561
4,955,863 A 9/1990 Walker et al.
4,968,306 A 11/1990 Huss et al.
4,978,334 A 12/1990 Toye et al.
4,995,866 A 2/1991 Amplatz et al.
5,053,004 A 10/1991 Markel et al.
5,069,673 A 12/1991 Shwab
5,380,292 A 1/1995 Wilson
5,562,626 A 10/1996 Sanpietro
5,699,801 A 12/1997 Atalar et al.
5,713,858 A 2/1998 Heruth et al.
5,720,720 A 2/1998 Laske et al.
5,722,985 A 3/1998 Pettus
5,792,144 A 8/1998 Fischell et al.
5,795,332 A 8/1998 Lucas et al.
5,833,662 A 11/1998 Stevens
5,851,203 A 12/1998 Van
5,857,999 A 1/1999 Quick et al.
5,871,470 A 2/1999 Mcwha
5,902,282 A 5/1999 Balbierz
5,919,171 A 7/1999 Kira et al.
5,928,145 A 7/1999 Ocali et al.
5,935,122 A 8/1999 Fourkas et al.
6,020,196 A 2/2000 Hu et al.
6,026,316 A 2/2000 Kucharczyk et al.
6,030,369 A 2/2000 Engelson et al.
6,042,579 A 3/2000 Elsberry et al.
6,050,992 A 4/2000 Nichols
6,093,180 A 7/2000 Elsberry
6,159,195 A 12/2000 Ha et al.
6,167,311 A 12/2000 Rezai
6,186,986 B1 2/2001 Berg et al.
6,231,591 B1 5/2001 Desai
6,263,229 B1 7/2001 Atalar et al.
6,284,971 B1 9/2001 Atalar et al.
RE37,410 E 10/2001 Brem et al.
6,309,634 B1 10/2001 Bankiewicz et al.
6,336,915 B1 1/2002 Scarfone et al.
6,356,786 B1 3/2002 Rezai et al.
6,405,079 B1 6/2002 Ansarinia
6,438,423 B1 8/2002 Rezai et al.
6,454,774 B1 9/2002 Fleckenstein
6,461,296 B1 10/2002 Desai
6,524,299 B1 2/2003 Tran et al.
6,526,318 B1 2/2003 Ansarinia
6,533,751 B2 3/2003 Cragg et al.
6,539,263 B1 3/2003 Schiff et al.
6,551,290 B1 4/2003 Elsberry et al.
6,585,694 B1 7/2003 Smith et al.
6,606,513 B2 8/2003 Lardo et al.
6,609,030 B1 8/2003 Rezai et al.
6,628,980 B2 9/2003 Atalar et al.
6,641,555 B1 11/2003 Botich et al.
6,641,564 B1 11/2003 Kraus
6,675,033 B1 1/2004 Lardo et al.
6,689,142 B1 2/2004 Tremaglio et al.
6,701,176 B1 3/2004 Halperin et al.
6,708,064 B2 3/2004 Rezai
6,904,307 B2 6/2005 Karmarkar et al.
7,037,295 B2 5/2006 Tiernan et al.
7,182,944 B2 2/2007 Bankiewicz
7,329,262 B2 2/2008 Gill
7,341,577 B2 3/2008 Gill
7,351,239 B2 4/2008 Gill
7,371,225 B2 5/2008 Oldfield et al.
7,780,692 B2 8/2010 Nance et al.
7,815,623 B2 10/2010 Bankiewicz et al.
7,892,203 B2 2/2011 Lenker et al.
7,951,110 B2 5/2011 Bishop et al.
7,984,929 B2 7/2011 Gill
8,128,600 B2 3/2012 Gill
8,175,677 B2 5/2012 Sayler et al.
8,195,272 B2 6/2012 Piferi et al.
8,315,689 B2 11/2012 Jenkins et al.
8,340,743 B2 12/2012 Jenkins et al.
8,348,892 B2 1/2013 Lenker et al.
8,374,677 B2 2/2013 Piferi et al.
8,597,277 B2 12/2013 Lenker et al.
8,827,987 B2 9/2014 Fielder et al.
8,900,214 B2 12/2014 Nance et al.
9,044,577 B2 6/2015 Bishop et al.
9,050,419 B2 6/2015 Farnan
9,452,241 B2 9/2016 Gill et al.
9,498,575 B2 11/2016 Flores
9,572,928 B2 2/2017 Shifflette et al.
9,610,048 B2 4/2017 Vij et al.
9,891,296 B2 2/2018 Piferi
10,105,485 B2 10/2018 Piferi et al.
10,576,247 B2 3/2020 Flores et al.
10,786,325 B1 9/2020 Osa
10,905,497 B2 2/2021 Pandey et al.
11,022,664 B2 6/2021 Piferi
2002/0052576 A1 5/2002 Massengale
2002/0087152 A1 7/2002 Mikus et al.
2002/0091372 A1 7/2002 Cragg et al.
2002/0095081 A1 7/2002 Vilsmeier
2002/0114780 A1 8/2002 Bankiewicz et al.
2002/0141980 A1 10/2002 Bankiewicz et al.
2002/0183763 A1 12/2002 Callol et al.
2003/0028095 A1 2/2003 Tulley et al.
2003/0050557 A1 3/2003 Susil et al.
2003/0073934 A1 4/2003 Putz
2003/0130575 A1 7/2003 Desai
2003/0216714 A1 11/2003 Gill
2004/0044329 A1 3/2004 Trudell
2004/0046557 A1 3/2004 Karmarkar et al.
2004/0064098 A1 4/2004 Cuschieri et al.
2004/0068190 A1 4/2004 Cespedes
2004/0092879 A1 5/2004 Kraus et al.
2004/0199129 A1 10/2004 Dimatteo
2004/0209810 A1 10/2004 Gill et al.
2004/0215162 A1 10/2004 Putz
2004/0249261 A1 12/2004 Torchia et al.
2005/0004504 A1 1/2005 Frye et al.
2005/0112065 A1 5/2005 Drummond et al.
2005/0148865 A1 7/2005 Weber
2005/0154297 A1 7/2005 Gill
2005/0228286 A1 * 10/2005 Messerly ............... A61B 8/445 600/459

(56) References Cited

U.S. PATENT DOCUMENTS

| | | | |
|---|---|---|---|
| 2005/0256503 | A1 | 11/2005 | Hall |
| 2005/0277889 | A1 | 12/2005 | Neidert et al. |
| 2006/0052750 | A1 | 3/2006 | Lenker et al. |
| 2006/0073101 | A1 | 4/2006 | Oldfield et al. |
| 2006/0129126 | A1 | 6/2006 | Kaplitt et al. |
| 2006/0135945 | A1 | 6/2006 | Bankiewicz et al. |
| 2006/0217664 | A1 | 9/2006 | Hattler et al. |
| 2007/0088295 | A1 | 4/2007 | Bankiewicz |
| 2007/0110798 | A1 | 5/2007 | Drummond et al. |
| 2007/0167736 | A1 | 7/2007 | Dietz et al. |
| 2007/0179455 | A1 | 8/2007 | Geliebter et al. |
| 2007/0250021 | A1 | 10/2007 | Brimhall et al. |
| 2007/0254842 | A1 | 11/2007 | Bankiewicz |
| 2007/0255275 | A1 * | 11/2007 | Skakoon .............. A61N 1/0539 606/41 |
| 2008/0103456 | A1 | 5/2008 | Johnson et al. |
| 2008/0119821 | A1 | 5/2008 | Agnihotri et al. |
| 2008/0215008 | A1 | 9/2008 | Nance et al. |
| 2008/0228168 | A1 | 9/2008 | Mittermeyer et al. |
| 2008/0319377 | A1 | 12/2008 | Keenan |
| 2009/0030400 | A1 | 1/2009 | Bose et al. |
| 2009/0082783 | A1 | 3/2009 | Piferi |
| 2009/0088695 | A1 | 4/2009 | Kapur et al. |
| 2009/0088730 | A1 | 4/2009 | Hoofnagle et al. |
| 2009/0112084 | A1 | 4/2009 | Piferi et al. |
| 2009/0118610 | A1 | 5/2009 | Karmarkar et al. |
| 2009/0143764 | A1 | 6/2009 | Nelson |
| 2009/0171184 | A1 | 7/2009 | Jenkins et al. |
| 2009/0177077 | A1 | 7/2009 | Piferi et al. |
| 2009/0198218 | A1 | 8/2009 | Gill et al. |
| 2009/0209937 | A1 | 8/2009 | Rogawski et al. |
| 2009/0281453 | A1 | 11/2009 | Tsonton et al. |
| 2010/0130958 | A1 | 5/2010 | Kang et al. |
| 2010/0198052 | A1 | 8/2010 | Jenkins et al. |
| 2010/0217228 | A1 | 8/2010 | Grahn et al. |
| 2010/0217236 | A1 | 8/2010 | Gill et al. |
| 2010/0228122 | A1 | 9/2010 | Keenan et al. |
| 2010/0317961 | A1 | 12/2010 | Jenkins et al. |
| 2010/0318061 | A1 | 12/2010 | Derrick et al. |
| 2010/0318064 | A1 | 12/2010 | Derrick et al. |
| 2011/0168176 | A1 | 7/2011 | Kholtchanski et al. |
| 2011/0282319 | A1 | 11/2011 | Gill |
| 2012/0123391 | A1 | 5/2012 | Gill et al. |
| 2012/0310182 | A1 | 12/2012 | Fielder et al. |
| 2013/0006095 | A1 | 1/2013 | Jenkins et al. |
| 2013/0030408 | A1 | 1/2013 | Piferi et al. |
| 2013/0150712 | A1 | 6/2013 | Field |
| 2013/0226094 | A1 | 8/2013 | Ahmed et al. |
| 2014/0163367 | A1 | 6/2014 | Eskuri |
| 2014/0171760 | A1 | 6/2014 | Singh et al. |
| 2014/0257168 | A1 | 9/2014 | Gill |
| 2014/0343500 | A1 | 11/2014 | Fielder et al. |
| 2015/0011938 | A1 | 1/2015 | Gill et al. |
| 2015/0080708 | A1 | 3/2015 | Piferi |
| 2015/0080814 | A1 | 3/2015 | Lambert et al. |
| 2015/0374908 | A1 | 12/2015 | Piferi |
| 2016/0074626 | A1 | 3/2016 | Weadock et al. |
| 2016/0100895 | A1 | 4/2016 | Piferi et al. |
| 2016/0213312 | A1 | 7/2016 | Singh et al. |
| 2016/0346505 | A1 | 12/2016 | Gill et al. |
| 2017/0056617 | A1 | 3/2017 | Thomson et al. |
| 2017/0197017 | A1 | 7/2017 | Martin |
| 2017/0232229 | A1 | 8/2017 | Flores et al. |
| 2018/0303560 | A1 | 10/2018 | Pandey et al. |
| 2019/0255282 | A1 | 8/2019 | Inukai et al. |
| 2019/0282320 | A1 | 9/2019 | Patwardhan et al. |
| 2019/0343496 | A1 | 11/2019 | Daly et al. |
| 2019/0346516 | A1 | 11/2019 | Piferi |
| 2020/0147299 | A1 | 5/2020 | Piferi |
| 2020/0229889 | A1 | 7/2020 | Kells et al. |
| 2020/0230361 | A1 | 7/2020 | Nelson et al. |
| 2021/0100977 | A1 | 4/2021 | Piferi |
| 2021/0187188 | A1 | 6/2021 | Daly et al. |
| 2021/0318397 | A1 | 10/2021 | Piferi |
| 2021/0361318 | A1 | 11/2021 | Patzke et al. |
| 2023/0310799 | A1 | 10/2023 | Piferi |

FOREIGN PATENT DOCUMENTS

| | | | |
|---|---|---|---|
| EP | 1029509 | A1 | 8/2000 |
| EP | 1334740 | A1 | 8/2003 |
| EP | 1482851 | A1 | 12/2004 |
| EP | 1491154 | A1 | 12/2004 |
| EP | 2558154 | A2 | 2/2013 |
| GB | 1255551 | A | 12/1971 |
| JP | 2002509767 | A | 4/2002 |
| JP | 2004147830 | A | 5/2004 |
| WO | 9904849 | A1 | 2/1999 |
| WO | 9949909 | A2 | 10/1999 |
| WO | 9949909 | A3 | 11/1999 |
| WO | 02053205 | A2 | 7/2002 |
| WO | 03077785 | A1 | 9/2003 |
| WO | 2004031348 | A2 | 4/2004 |
| WO | 2008020237 | A2 | 2/2008 |
| WO | 2008020241 | A2 | 2/2008 |
| WO | 2008144585 | A1 | 11/2008 |
| WO | 2008144775 | A1 | 11/2008 |
| WO | 2009042135 | A2 | 4/2009 |
| WO | 2009047490 | A2 | 4/2009 |
| WO | 2009066130 | A1 | 5/2009 |
| WO | 2009101397 | A1 | 8/2009 |
| WO | 2010040970 | A2 | 4/2010 |
| WO | 2011098768 | A1 | 8/2011 |
| WO | 2011098769 | A1 | 8/2011 |
| WO | 2011130107 | A2 | 10/2011 |
| WO | 2012178169 | A2 | 12/2012 |
| WO | 2013050148 | A1 | 4/2013 |
| WO | 2014089373 | A1 | 6/2014 |
| WO | 2019030761 | A1 | 2/2019 |

OTHER PUBLICATIONS

Chen et al. "Surface properties, more than size, limiting convective distribution of virus-sized particles and viruses in the central nervous system" Journal of Neurosurgery 103:311-319 (2005).

Cunningham et al. "Distribution of AAV-TK following intracranial convection-enhanced delivery into rats" Cell Transplantation 9(5):585-594 (2000) (Abstract Only).

Groothuis, Dennis R. "The blood-brain and blood-tumor barriers: A review of strategies for increasing drug delivery" Neuro-Oncology 2:45-59 (2000).

Hadaczek et al. "Convection-Enhanced Delivery of Adeno-Associated Virus Type 2 (AAV2) into the Striatum and Transport of AAV2 Within Monkey Brain" Human Gene Therapy 17:291-302 (2006).

Hadaczek et al. "The 'Perivascular Pump' Driven by Arterial Pulsation is a Powerful Mechanism for the Distribution of Therapeutic molecules within the Brain" Molecular Therapy 14(1):69-78 (2006).

Hanley et al. "Safety and efficacy of minimally invasive surgery plus recombinant tissue plasminogen activator in intracerebral haemorrhage evacuation (MISTIE): a randomised, phase 2 trial" The Lancet Neurology, 15(12):1228-1237 (2016).

Krauze et al. "Real-time Imaging and Quantification of Brain Delivery of Liposomes" Pharmaceutical Research 23(11):2493-2504 (2006).

Krauze et al. "Reflux-free cannula for convection-enhanced high speed delivery of therapeutic agents" Journal of Neurosurgery 103:923-929 (2005).

Aske et al. "Chronic interstitial infusion of protein to primate brain: determination of drug distribution and clearance with single-photon emission computerized tomography imaging" Journal of Neurosurgery 87:586-594 (1997).

Lieberman et al. "Convection-enhanced distribution of large molecules in gray matter during interstitial drug infusion" Journal of Neurosurgery 82:1021-1029 (1995).

Lonser et al. "Successful and safe perfusion of the primate brainstem: in vivo magnetic resonance imaging of macromolecular distribution during infusion" Journal of Neurosurgery 97:905-913 (2002).

(56) References Cited

OTHER PUBLICATIONS

Mamot et al. "Extensive distribution of liposomes in rodent brains and brain tumors following convection-enhanced delivery" Journal of Neuro-Oncology 68:1-9 (2004).
Mardor et al. "Monitoring Response to Convection-enhanced Taxol Delivery in Brain Tumor Patients Using Diffusion-weighted Magnetic Resonance Imaging" Cancer Research 61:4971-4973 (2001).
Marshall et al. "Biocompatibility of Cardiovascular Gene Delivery Catheters with Adenovirus Vectors: An Important Determinant of the Efficiency of Cardiovascular Gene Transfer" Molecular Therapy 1(5):423-429 (2000).
Morrison et al. "Focal delivery during direct infusion to brain: role of flow rate, catheter diameter, and tissue mechanics" American Journal of Physiology—Regulatory, Integrative and Comparative Physiology 277:R1218-R1229 (1999).
Morrison et al. "High-flow microinfusion: tissue penetration and pharmacodynamics" American Journal of Physiology—Regulatory, Integrative and Comparative Physiology 266:R292-R305 (1994).
Mould et al. "Minimally Invasive Surgery plus rt-PA for Intracerebral Hemorrhage Evacuation (MISTIE) Decreases Perihematomal Edema" Stroke, 44(3):627-634 (2013).
Naimark et al. "Adenovirus-Catheter Compatibility Increases Gene Expression After Delivery to Porcine Myocardium" Human Gene Therapy 14:161-166 (2003).
Pardridge, William M. "Drug Delivery to the Brain" Journal of Cerebral Blood Flow and Metabolism 17:713-731 (1997).
Pardridge, William M. "The Blood-Brain Barrier: Bottleneck in Brain Drug Development" NeuroRx: The Journal of the American Society for Experimental Neuro Therapeutics 2:3-14 (2005).
Patel et al. "Intraputamenal Infusion of Glial Cell Line-Derived Neurotrophic Factor in PD: A Two-Year Outcome Study" Annals of Neurology 57:298-302 (2005).
Qureshi et al. "Multicolumn Infusion of Gene Therapy Cells into Human Brain Tumors: Technical Report" Neurosurgery 46(3):663-669 (2000) (Abstract Only).
Richardson et al. "Interventional MRI-guided Putaminal Delivery of AAV2-GDNF for a Planned Clinical Trial in Parkinson's Disease" Molecular Therapy 19(6):1048-1057 (2011).
Rogawski, Michael A. "Convection-Enhanced Delivery in the Treatment of Epilepsy" Neurotherapeutics: The Journal of the American Society for Experimental Neuro Therapeutics 6:344-351 (2009).
Saito et al. "Distribution of Liposomes into Brain and Rat Brain Tumor Models by Convection-Enhanced Delivery Monitored with Magnetic Resonance Imaging" Cancer Research 64:2572-2579 (2004).
Tsui et al. "Stability of Adenoviral Vectors Following Catheter Delivery" Molecular Therapy 3(1):122-125 (2001).
Vogelbaum, Michael A. "Convection enhanced delivery for the treatment of malignant gliomas: symposium review" Journal of Neuro-Oncology 73:57-69 (2005).
Bankiewicz, Krys S., et al., "Convection-Enhanced Delivery of AAV Vector in Parkinsonian Monkeys; In Vivo Detection of Gene Expression and Restoration of Dopaminergic Function Using Prodrug Approach", Experimental Neurology, 164(1), 2000, 2-14.
Chen, Michael Y., et al., "Variables affecting convection-enhanced delivery to the striatum: a systematic examination of rate of infusion, cannula size, infusate concentration, and tissue-cannula sealing time", Journal of Neurosurgery, 90(2), 1999, 315-320.
Saito, Ryuta , et al., "Convection-enhanced delivery of tumor necrosis factor-related apoptosis-inducing ligand with systemic administration of temozolomide prolongs survival in an intracranial glioblastoma xenograft model", Cancer Research, 64(19), 2004, 6858-6862.
Westphal, Manfred , et al., "Perspectives of cellular and molecular neurosurgery", Journal of Neuro-Oncology, 70(2), 2004, 255-269.
International Search Report and the Written Opinion of the International Searching Authority corresponding to International Patent Application No. PCT/US2023/014009 (16 pages) (mailed May 10, 2023).
"Peripheral Interventions", Product Catalog, Boston Scientific, pp. 20-21 (Apr. 2020).
Non-Final Office Action issued for U.S. Appl. No. 18/175,638, mailed Jan. 5, 2026.
Final Office Action issued for U.S. Appl. No. 18/175,638, mailed May 11, 2026.

* cited by examiner

SURGICAL THERAPY SYSTEMS AND RELATED METHODS

RELATED APPLICATIONS

This patent application claims the benefit of and priority to U.S. Provisional Patent Application Ser. No. 63/322,257, filed Mar. 22, 2022, the contents of which are hereby incorporated by reference as if recited in full herein.

FIELD OF THE INVENTION

The present invention relates generally to medical devices and systems and, more particularly, to devices and systems for delivering a therapy in vivo and may be particularly suitable for MRI-guided deep brain procedures.

BACKGROUND

Various medical procedures require that a substance be aspirated or delivered into a prescribed region of a patient, such as to a deep brain target. It may be important or critical that the substance be delivered with high accuracy to the target region in the patient, sometimes over a relatively long delivery period or periods.

In the past, a rigid cannula has been used with a surgical navigation frame attached to a skull of a patient defining a rigid coupling that extends into the brain. See, U.S. Pat. No. 10,905,497, the content of which is hereby incorporated by reference as if recited in full herein. While the rigid cannula configuration provides a secure delivery path for the medical procedure, the patient must remain in a stationary position to avoid movement of the brain relative to the surgical navigation frame and the rigid cannula inside the brain.

Referring to FIGS. 1A, 1B, in other known systems, a delivery system with a rigid and relatively long cylindrical (annular) rigid ceramic stylet member 10 positioned between an outer body 11 of a fluid delivery catheter and an inner body 12 of the flexible delivery catheter that has been used to position the flexible delivery catheter during an image-guided medical procedure. The inner and outer bodies 11, 12 of the flexible delivery catheter do not move relative to each other as they are affixed together at a distal end portion and can be anchored to a bolt 13 attached to the skull using a bolt cap 14. However, the rigid ceramic stylet member 10 must be slidably removed from the flexible catheter and a luer fitting then installed at a proximal portion during the medical procedure.

In yet other known prior art surgical navigation systems, peel-away guide sheaths have been used with surgical navigation frames during surgical image-guided procedures to implant long flexible leads such as deep brain stimulation leads.

There is a need for alternate therapy systems that can accommodate longer duration procedures and/or patient movement without requiring peel-away sheaths and that avoids any in-field assembly of a luer connector onto a component such as flexible tubing.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention provide a delivery system that includes a sheath assembly that can couple to a bolt attached to a skull of a patient and that can remain implanted during a medical procedure that can last several hours or even days or more chronically. The delivery system includes a seal member that resides in the bolt and can cooperate with the bolt and a bolt nut to define a fluid tight seal thereat. The bolt has an axially extending through hole. The sheath assembly has a through lumen sized and configured to slidably receive a therapy device to position a distal end of the therapy device at a defined intra-brain target.

The therapy device can be a flexible catheter.

The therapy device can include a laser.

The therapy device can include stimulation electrodes.

Embodiments of the invention are directed to delivery systems with a sheath assembly that cooperate with surgical fluid transfer devices for transferring fluid to or from a subject and may be particularly suitable for infusion or other drug delivery procedures to a target site(s) in the brain.

The devices may be MRI-compatible.

Embodiments of the present invention provide a medical system that includes a sheath assembly with a guide sheath having a proximal end and an opposing distal end and with a lumen extending therethrough. The proximal end includes a shoulder that extends radially outward from the lumen. The medical system also includes a bolt configured to threadably engage a skull of a patient. The bolt has an open channel that extends axially therethrough. The guide sheath is configured to reside in the open channel of the bolt with the distal end residing distally of the bolt. The medical system also includes a seal member inside the bolt adjacent the shoulder of the guide sheath and a bolt nut configured to couple to the bolt.

The proximal end of the sheath assembly can terminate inside the bolt.

The bolt nut can have a distal portion that is configured to apply a clamping force against the seal member.

The seal member can include or be defined by a silicone O-ring.

The guide sheath can have a length that is in a range of about 1 cm to about 12 cm.

The guide sheath can be configured to be cut to length at a location distal to the shoulder and seal member.

The sheath assembly can be provided as a set of sheath assemblies, each sheath assembly can have a sheath with a different length to thereby allow a user to select an appropriate sheath assembly with a guide sheath having a desired length to extend to a target site in the patient for a medical procedure.

The medical system can further include a stylet that has increased rigidity relative to the guide sheath. The stylet can be releasably and slidably coupled to the sheath assembly.

The stylet can have externally visible indicia of length or markings in distance increments, optionally the stylet can have a ceramic body.

The stylet can have an end portion with a shoulder having an open, outer facing channel that can be configured to slidably receive the distal end of the sheath to thereby profile and/or shape the distal end of the sheath.

The guide sheath can have an outer diameter in a range of 2 F to 8 F, with a wall thickness in a range of about 0.002 inches to about 0.025 inches to thereby have a flexible body that can remain in position to a target and deflect (relative to a bolt affixed to the skull and/or the skull) in response to a deflection load applied by brain tissue during a brain positional shift when implanted. The deflection load can be small as can the positional movement of the guide sheath (and catheter held therein) such as in a range of 1 ounce to 3 ounces.

The guide sheath can be formed of medical grade polyethylene, polyimide, PEEK, PEBAX or TEFLON.

The medical system can include a therapy device that extends through the guide sheath. The therapy device and the guide sheath can be sufficiently flexible when coupled together to be able to shift in concert together in response to brain shift when implanted.

The medical system can also include an insertion tool assembly with an open through channel configured to attach the sheath assembly to the bolt prior to coupling the bolt nut to the bolt. The stylet can releasably extend through the open through channel of the insertion tool assembly and can concurrently releasably extend through the lumen of the sheath assembly to provide rigidity during intrabody placement. When assembled, a distal end of the insertion tool assembly can abut the sheath assembly whereby the insertion tool places the sheath assembly in the bolt.

The seal member can be attached to the shoulder of the sheath assembly.

The medical system can also include a flexible catheter that can be configured to with a portion that slidably extends through the sheath assembly with sufficient flexibility to be able to bend at an angle of 45-90 degrees without breaking. The flexible catheter has axially opposed proximal and distal ends and a length sufficient to position the distal end internal to the patient outside the distal end of the guide sheath. The flexible catheter can have a leur connector on the proximal end thereof.

The flexible catheter can have an external segment that is configured to reside outside the patient comprising a first segment with a first outer diameter that merges into a second segment with a second, greater outer diameter, that is coupled to the luer connector at the proximal end. The flexible catheter can have a third segment that is configured to reside inside the patient. The third segment can merge into at least one stepped outer diameter segment at a distal end portion thereof that resides outside the guide sheath.

The first segment can be configured to be routed through a groove in the bolt and bolt cap at an angle that is about 90 degrees from an axially extending centerline of the guide sheath and a portion of the flexible catheter held distal to the bolt.

The medical system can also include a trajectory guide that is configured to reside over or attach to the patient. The trajectory guide can have a tower that is moveable to define a trajectory angle for a trajectory path to a target site in the brain. The insertion tool assembly can have a length sufficient to extend at least partially through the tower with a proximal end residing outside and more proximal to the tower.

The bolt nut can have threads that engage external threads on the bolt and the bolt nut can have a distal end that has a laterally extending width and/or radius that matches a laterally extending width and/or outer diameter of the seal member.

The bolt channel can define a seat for the shoulder of the sheath assembly. The bolt nut can cooperate with the bolt to clamp against the seal member to inhibit fluid leakage from the patient distal to the seal member.

Yet other embodiments are directed to an image-guided surgical system that includes: a surgical navigation trajectory guide with a tower that is moveable to define a trajectory angle; a sheath assembly with an elongate guide sheath having a proximal end and an opposing distal end and with an open through lumen extending therethrough. The proximal end has a radially outwardly extending shoulder. The system also includes a bolt configured to threadably engage a skull of a patient. The bolt has an open channel that extends axially therethrough. The guide sheath is configured to reside in the open channel of the bolt with the distal end residing distally of the bolt and with the proximal end terminating inside the bolt. The system also includes a bolt nut configured to couple to the bolt; a stylet releasably insertable through the sheath assembly and an insertion tool assembly with an open through channel, configured to attach the sheath assembly to the bolt prior to coupling the bolt nut to the bolt. The stylet releasably extends through the open through channel of the insertion tool assembly and concurrently releasably extends through the lumen of the guide sheath assembly. When assembled together, a distal end of the insertion tool assembly abuts the sheath assembly whereby the insertion tool places the sheath assembly in the bolt with the shoulder thereof or a seal member in the bolt against a seat inside the bolt. The insertion tool assembly has a length sufficient to extend at least partially through the tower with a proximal end residing outside and more proximal to the tower, The image guided surgical system can also include a sheath assembly calculation module that is configured to define a length of a sheath body needed to reach a target treatment site in a patient from a defined location on the bolt.

The image guided surgical system can further include a catheter with a luer connector configured to engage a length of flexible tubing to couple to a pump for delivery of a medical therapy.

The guide sheath assembly, the stylet, the bolt, the bolt cap and the insertion tool can all be MRI compatible devices provided in a kit for a medical procedure.

The image guided surgical system can also include a seal member in the bolt residing above or below or above and below the radially outwardly extending shoulder of the sheath assembly.

The seal member can be attached to the shoulder of the sheath assembly.

Yet other embodiments are directed to methods of providing a medical treatment and/or positioning surgical devices for delivering fluid to a target intrabody site. The methods include: providing a set of (optionally MRI compatible) components that include a sheath assembly with a guide sheath, a stylet configured to releasably couple to the sheath assembly, an insertion tool assembly, a bolt configured to attach to a skull, and a bolt nut; positioning a trajectory guide with a tower on or about a head of patient, the trajectory guide defining a trajectory axis into the patient to a target site; attaching the bolt to a skull of the patient at a brain entry point of the trajectory axis; inserting the sheath assembly, insertion tool assembly and stylet, coupled together as an assembly, through an open channel of the tower and into the bolt; removing the insertion tool assembly from the tower with or separately from removing the stylet from the sheath assembly; then coupling a bolt nut to the bolt with a proximal end portion thereof facing and adjacent, optionally residing against, a shoulder of the sheath assembly in the bolt and/or a seal member in the bolt.

The method can include, after the coupling: inserting a catheter into the guide sheath so that a distal end thereof resides outside the guide sheath assembly at the target site; tightening the bolt nut to the bolt; attaching a bolt cap to the bolt nut; and delivering a therapeutic agent to the target site from the catheter The inserting, removing and coupling can be carried out while the patient is in a magnet of an MR Scanner during an MRI guided surgical procedure.

The method can further include before the inserting, cutting the guide sheath to have a desired length to reach the target site.

The cutting can be carried out while the stylet is in the guide sheath, optionally with the stylet in a reverse orientation from the inserting orientation The method can also include rotating a cut end of the guide sheath in a channel of a shoulder of the stylet and/or rotating the shoulder with the cut end of the guide sheath in the channel to profile and/or shape the cut end of the guide sheath The method can include routing a segment of the catheter out of a channel defined by a cooperating groove of the bolt cap and a slot of the bolt nut so that the segment bends at about 90 degrees from an angle of another segment of the catheter that resides distal of the bolt.

The catheter can be a flexible catheter that can bend at least 30 degrees from an axially extending centerline thereof. The delivering can be carried out over at least a two-hour period and the patient is not required to remain stationary. The flexible catheter portion inside the brain can be able to move (shift) in response to (with) brain shift movement.

The delivering can be carried out, at least in part, after the trajectory guide is taken away or removed.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

DETAILED DESCRIPTION

Figure 1A:
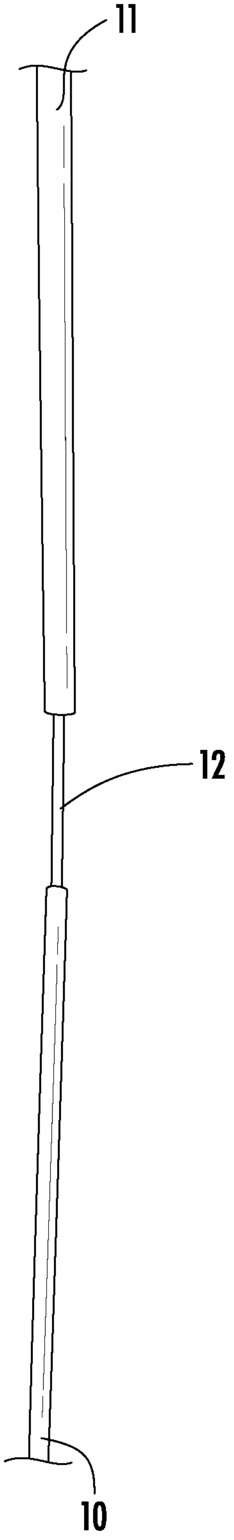
FIG. 1A PRIOR ART
FIG. 1A is a digital photograph of a portion of a prior art therapy system having a slidably removable cylindrical/annular stylet between an inner needle/flexible catheter to provide rigidity during intrabody placement.
Figure 1B:
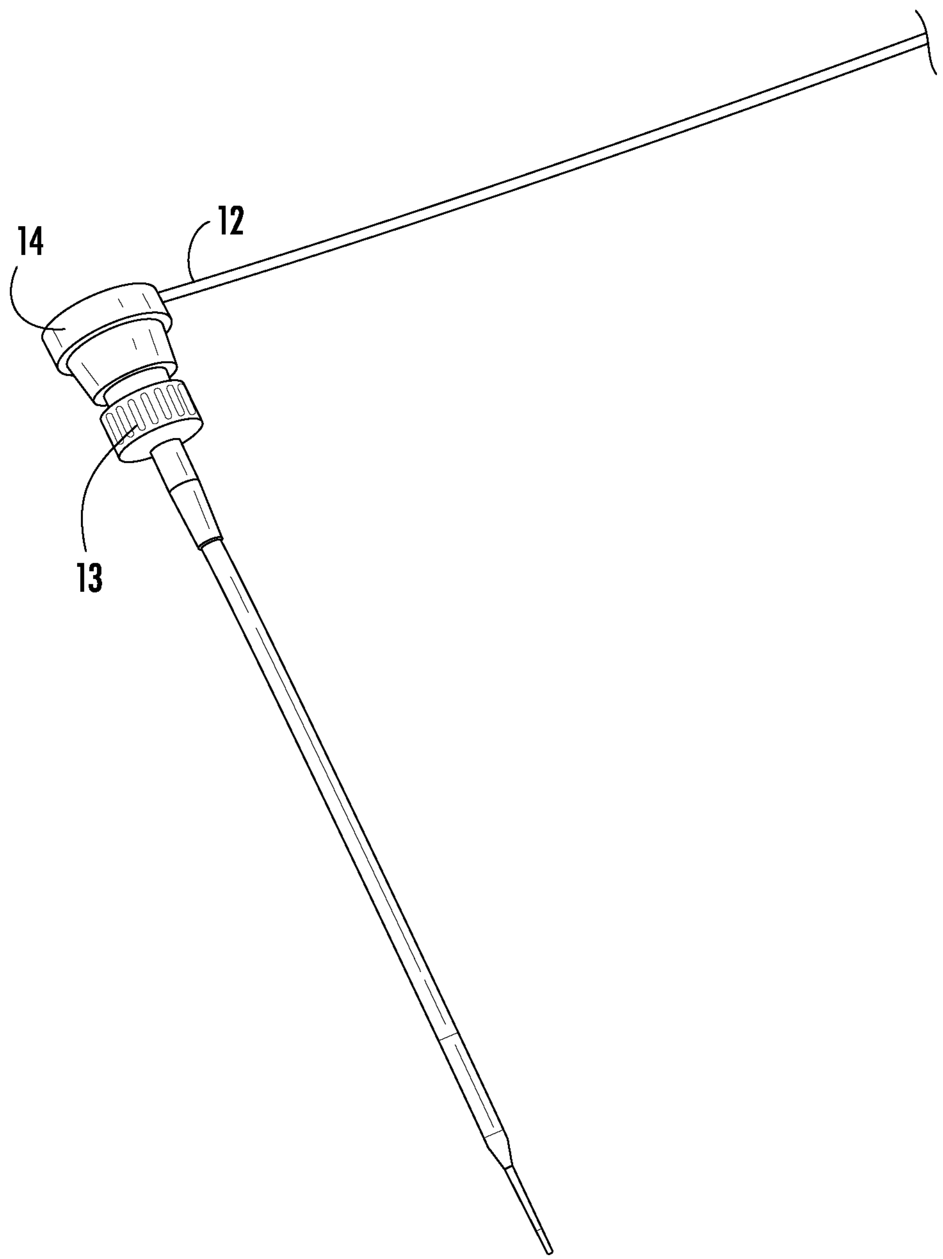
FIG. 1B PRIOR ART
FIG. 1B is a digital photograph of a prior art system showing a catheter held in position using a bolt, a bolt nut and a bolt nut cap.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The abbreviations "FIG." and "Fig." are used interchangeably with the word "Figure" to refer to the drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/− twenty percent (20%).

The term "monolithic" means that the component (e.g., needle) is formed of a single uniform material.

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T, such as 2.0 T and 3.0 T, for example.

The term "near real time" refers to both low latency and high frame rate. Latency is generally measured as the time from when an event occurs to display of the event (total processing time). For near "real-time" imaging, the frame rate is typically between about 1 fps to about 20 fps, and in some embodiments, between about 3 fps to about 7 fps. The low latency required to be considered "near real time" is generally less than or equal to about 1 second. With respect to imaging, visualizations using near real time MR image data can be presented with a low latency, typically within between about 0.01 ms to less than about 1 second, and with a frame rate that is typically between about 1-20 fps. The MRI-guided interventional system can use the image signal data to dynamically present anatomy and one or more intrabody devices in the visualization in near real-time.

The term "sterile," as used herein, means that a device, kit, and/or packaging meets or exceeds medical/surgical cleanliness guidelines, and typically is free from live bacteria or other microorganisms.

The term "semi-rigid" refers to devices that have sufficient rigidity to have a self-supporting fixed shape (typically straight linear cylindrical shapes) in the absence of applied bending forces but have sufficient flexibility to be able to bend or deflect without breaking in response to normal forces applied during normal use.

The term "flexible" refers to devices that have less rigidity than semi-rigid devices.

The subject can be any subject and may be particularly suitable for animal and/or human subjects for e.g., animal studies and/or veterinarian or human treatments.

Some embodiments provide therapy delivery systems that cooperate with therapy devices that deliver a substance to or withdraw a fluid from a target intrabody region such as, for example, a brain.

Embodiments of the invention can be used to position a therapy device such as a flexible catheter, a laser, or a stimulation electrode(s) in the brain.

Embodiments of the invention can deliver therapies to the spine.

Embodiments of the invention can deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat a patient with one or more tumors.

The term "fluid" with respect to fluid being withdrawn from a subject refers to soft tissue, foreign matter, biological matter including cellular material and liquid in a subject.

The term "substance," as used herein, refers to a gas or liquid for delivery to a subject for treating or facilitating diagnosis of a condition and can include bions, stem cells or other target cells to site-specific regions in the body, such as neurological, nerves or other target sites and the like. In some embodiments, stem cells and/or other rebuilding cells or immune therapy products can be delivered into spine, brain or cardiac tissue. Embodiments of the invention can be used to transfer fluid to or from a heart wall via a minimally invasive Mill guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Embodiments of the present invention will now be described in further detail below with reference to the figures.

Figure 2:
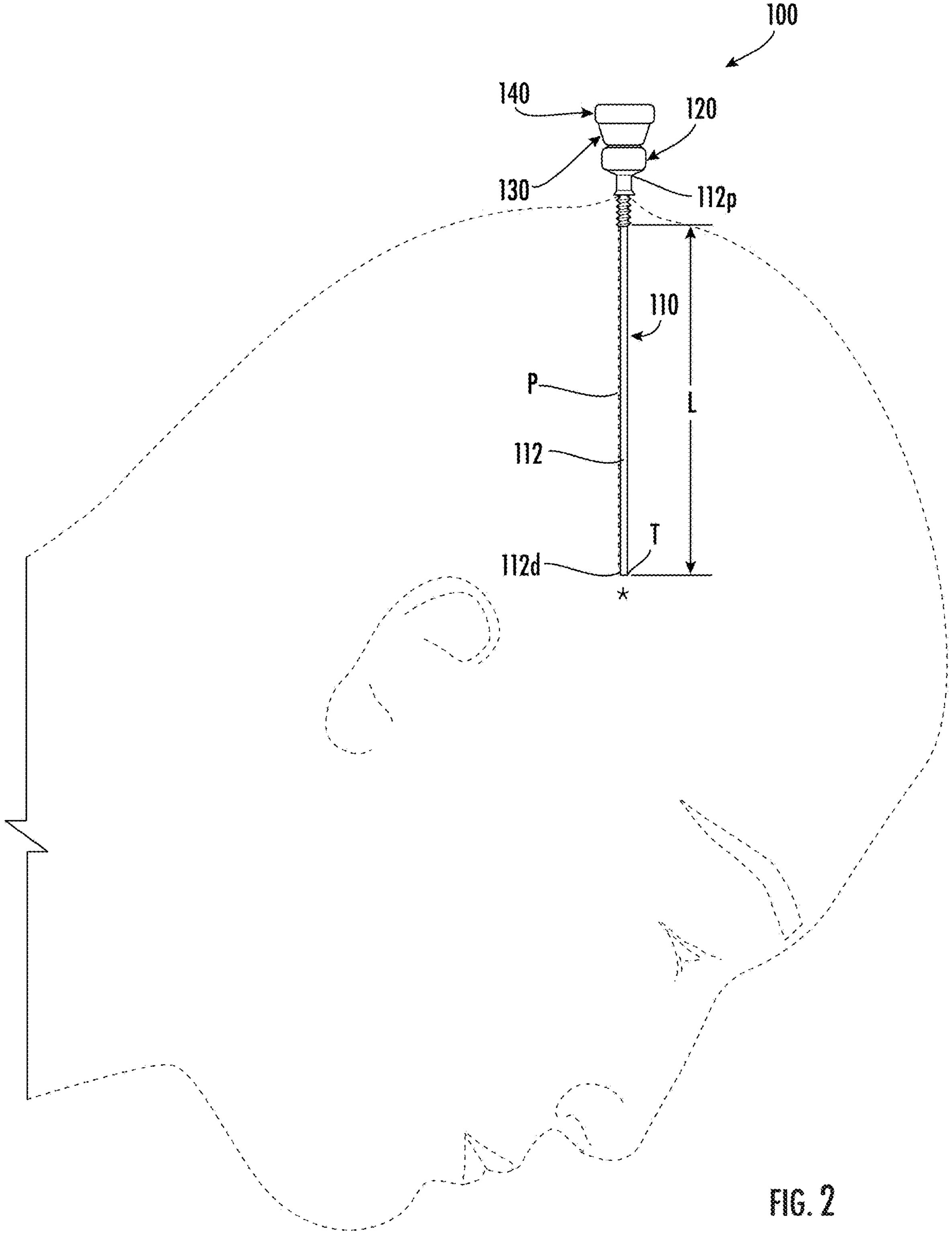
FIG. 2 is a schematic illustration of a delivery system in an example position of a brain of a patient and comprising a sheath assembly coupled to a bolt providing a trajectory path to a target site in the patient according to embodiments of the present invention.

FIG. 2 illustrates a therapy system 100 comprising a sheath assembly 110, a bolt 120, a bolt nut 130 and a bolt nut cap 140. As shown, the bolt 120 is screwed into the skull of a patient. The sheath assembly 110 has a guide sheath 112 that extends a distance L outside the bolt 120, distal to the bolt 120, to define a trajectory path P to a target intrabody site T. The guide sheath 112 has an open axially/longitudinally extending lumen 112*l*.

The length L of the sheath 112 may (and typically does) vary depending on the target site T and a patient. The length L may be in a range of about 1 cm to about 12 cm, in some embodiments. The length L can be about 1 cm, about 1.5 cm, about 2 cm, about 2.5 cm, about 3 cm, about 3.5 cm, about 4 cm, about 4.5 cm, about 5 cm, about 5.5 cm, about 6 cm, about 6.5 cm, about 7 cm, about 7.5 cm, about 8 cm, about 8.5 cm, about 9 cm, about 9.5 cm, about 10 cm, about 10.5 cm, about 11 cm, about 11.5 cm, or about 12 cm. The sheath assembly 110 can remain in position, coupled to the bolt 120 during successive medical therapies or over a relatively long single therapy of 2 hours or more. The guide sheath 112 of the sheath assembly 110 can have a distal end portion 112*d* and a proximal end portion 112*p*.

In some embodiments, the proximal end portion 112*p* of the guide sheath 112 can terminate inside the bolt 120.

Figure 5A:
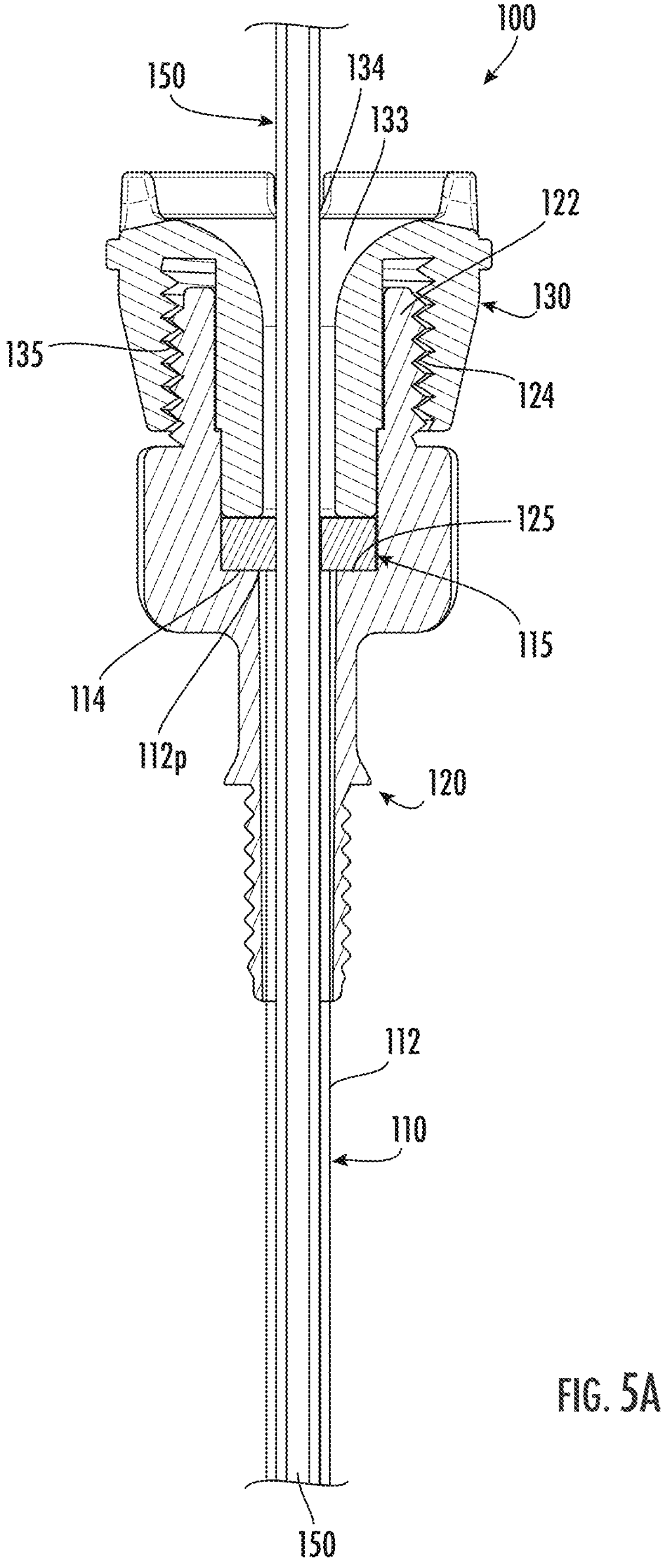
FIG. 5A is an enlarged, cross-sectional view of the delivery system with the coupled therapy device shown in FIG. 4A according to embodiments of the present invention.

As shown in FIG. 5A, the guide sheath 112 has a shoulder 114. The shoulder 114 is held directly or indirectly against a seat 125 formed in the bolt 120 by the bolt nut 130. The shoulder 114 can radially outwardly extend at the proximal end portion 112*p* of the guide sheath 112.

Figure 3B:
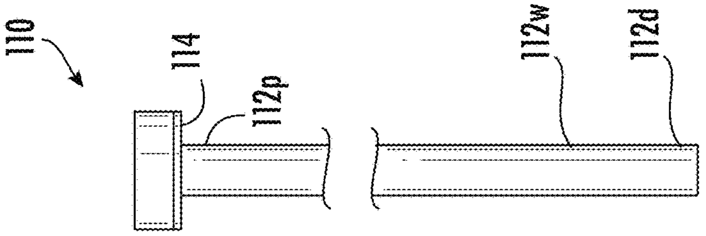
FIG. 3B is a side assembled view of the sheath assembly shown in FIG. 3A.
Figure 3A:
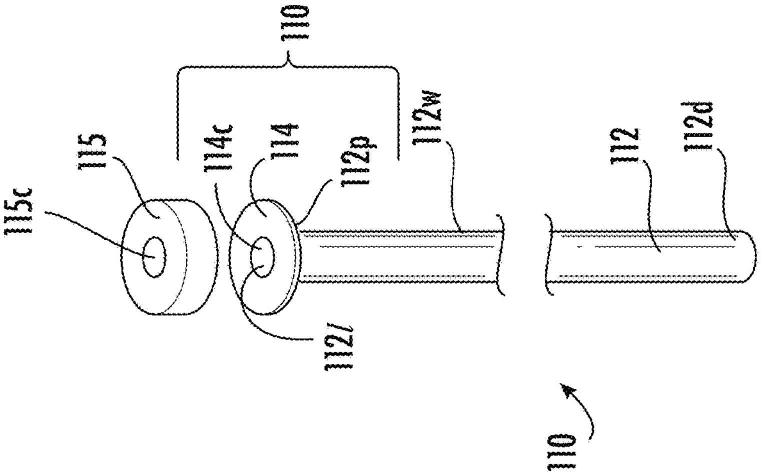
FIG. 3A is a side perspective, exploded view of an example sheath assembly according to embodiments of the present invention.
Figure 3C:
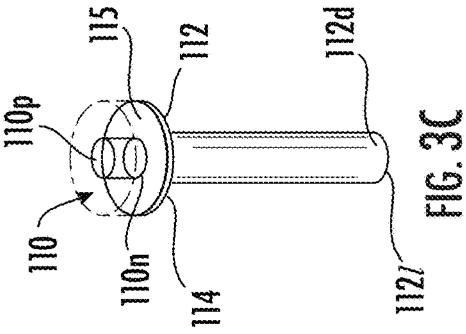
FIGS. 3C-3E are side perspective views of example alternate embodiments of the sheath assembly according to embodiments of the present invention.

Referring to FIGS. 3A, 3B, 4A and 5A, the therapy system 100 can include a seal member 115 that can reside in the bolt 120. As shown in FIGS. 3A-3C, the seal member 115 can reside adjacent and/or on the shoulder 114 at the proximal end portion 112*p* of the guide sheath 112. The seal member 115 and the shoulder 114 can have a center open channel 114*c*, 115*c*. The seal member 115 can comprise an O-ring, gasket or other seal member or combinations of seal members. In some particular embodiments, the seal member 115 comprises a silicone O-ring.

The bolt 120 comprises an open channel 122 (FIG. 5A, 5B, 14A, 14B) that extends axially therethrough. The guide sheath 112 is configured to reside in the open channel 122 of the bolt 120 with the distal end portion 112*d* residing distally of the bolt 120 and with the seal member 115 and shoulder 114 inside the bolt 120.

The seat 125 of the bolt 120 can define a trapping surface 125 that can directly or indirectly (e.g., through the shoulder 114) couple to the seal member 115.

FIGS. 3A and 3B illustrate that the seal member 115 can be attached to the guide sheath 112. The seal member 115 can be bonded or adhesively attached to the shoulder 114. The seal member 115 may also be over-molded onto the shoulder 114 or formed in other manners. The shoulder 114 can be injection molded with the guide sheath 112 or attached as a separate component. The shoulder 114 can be formed of a different material and/or in a different thickness than the wall 112*w* of the guide sheath 112.

FIG. 3C illustrates that the sheath assembly 110 can have a proximal end 110*p* with a neck 110*n* that projects above/extends above the shoulder 114 for a short distance and that can provide an alignment feature for ease of assembly of the seal member 115. The short distance can be configured so that the neck 110*n* terminates inside the bolt 120.

Figure 3D:
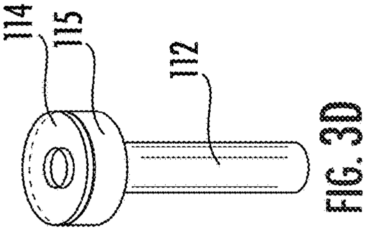

FIG. 3D illustrates that the sheath assembly 110 can be configured with the seal member 115 below the shoulder 114.

Figure 3E:
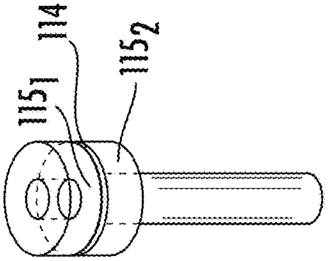

FIG. 3E illustrates that the sheath assembly 110 can be configured with a first seal member $\mathbf{115}_1$ above the shoulder 114 and a second seal member $\mathbf{115}_2$ below the shoulder 114.

Figure 5B:
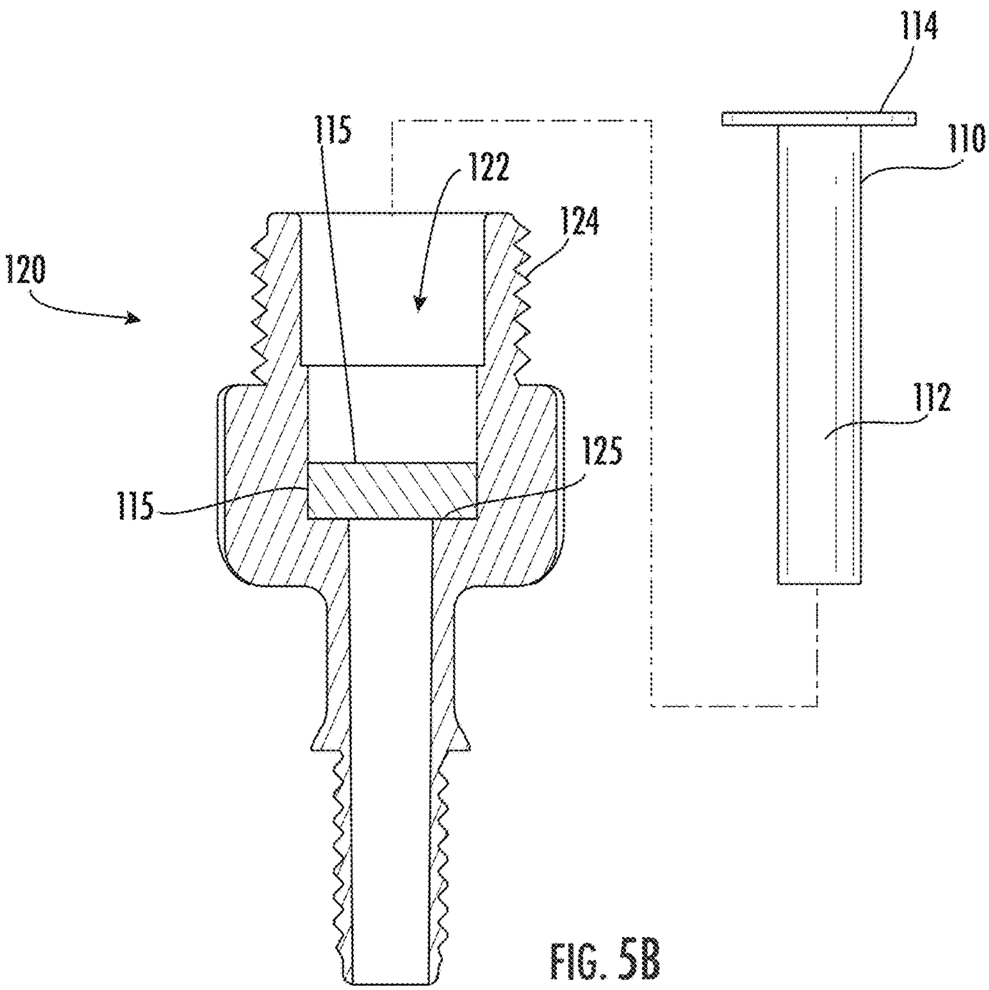
FIG. 5B is an enlarged, cross-sectional view of another example of a bolt and sheath assembly according to embodiments of the present invention.

FIG. 5B illustrates that the seal member 115 can be provided as a separate component from the sheath assembly 110. For example, the seal member 115 may be pre-attached to the seal member seat/trapping surface 125 and provided as a sub-assembly in a kit 375 (FIG. 19) of cooperating components for the surgical procedure, e.g., a kit with the sheath assembly 110, the bolt 120 and the bolt nut 130 and potentially other components as will be discussed below.

FIG. 5A shows the shoulder 114 below the seal member 115 in the bolt 120.

FIG. 5B also shows that the sheath assembly 110 can be configured to place the shoulder 114 above the seal member 115 in the bolt 120 rather than below.

Figure 5C:
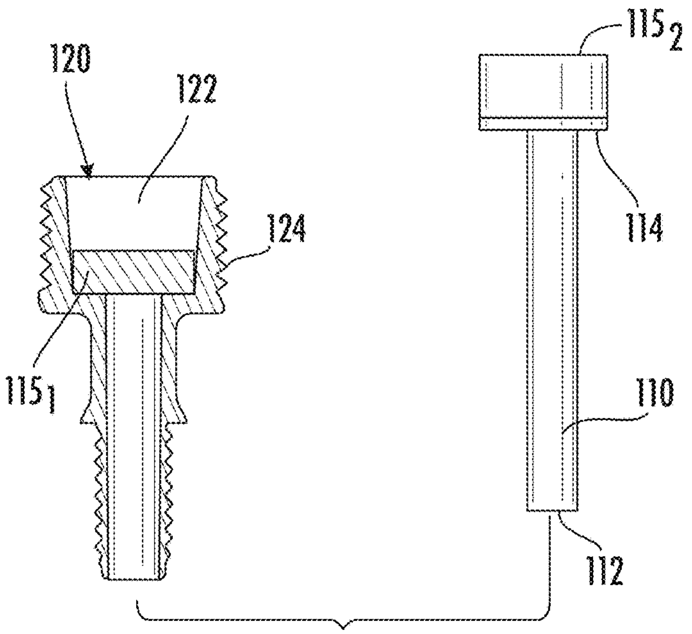
FIG. 5C is an enlarged, cross-sectional view of yet another example of a bolt and sheath assembly according to embodiments of the present invention.

FIG. 5C illustrates that a first seal member $\mathbf{115}_1$ can be positioned against the seal member seat/trapping surface 125 in the open channel 122 of the bolt 120 and the sheath assembly 110 can position a second seal member $\mathbf{115}_2$ above the shoulder 114 so that, in position, the shoulder 114 resides between the first and second seal members $\mathbf{115}_1$, $\mathbf{115}_2$.

The wall 112*w* of the guide sheath 112 can have a wall thickness in a range of 0.002 inches to about 0.025 inches to thereby have a semi-rigid or flexible body.

In some embodiments, the guide sheath 112 can have an outer diameter of in a range of 2 F to 8 F.

The guide sheath 112 can be formed of medical grade polyethylene, polyimide, PEEK, PEBAX or TEFLON.

The stylet 210 can have a solid body devoid of a through channel (such as shown in the prior art stylet of FIG. 1A) and as the stylet 210 is serially interchangeably positionable in the lumen 112*l* of the guide sheath 112, the inner diameter of the guide sheath 112 can more closely match the outer diameter of the internal segment of the flexible catheter 150. This may allow for more precise positioning or tighter tolerances along the trajectory path, such as spacing in a range of about 0.001-0.002 inch per side or in an annular clearance space.

Figure 4A:
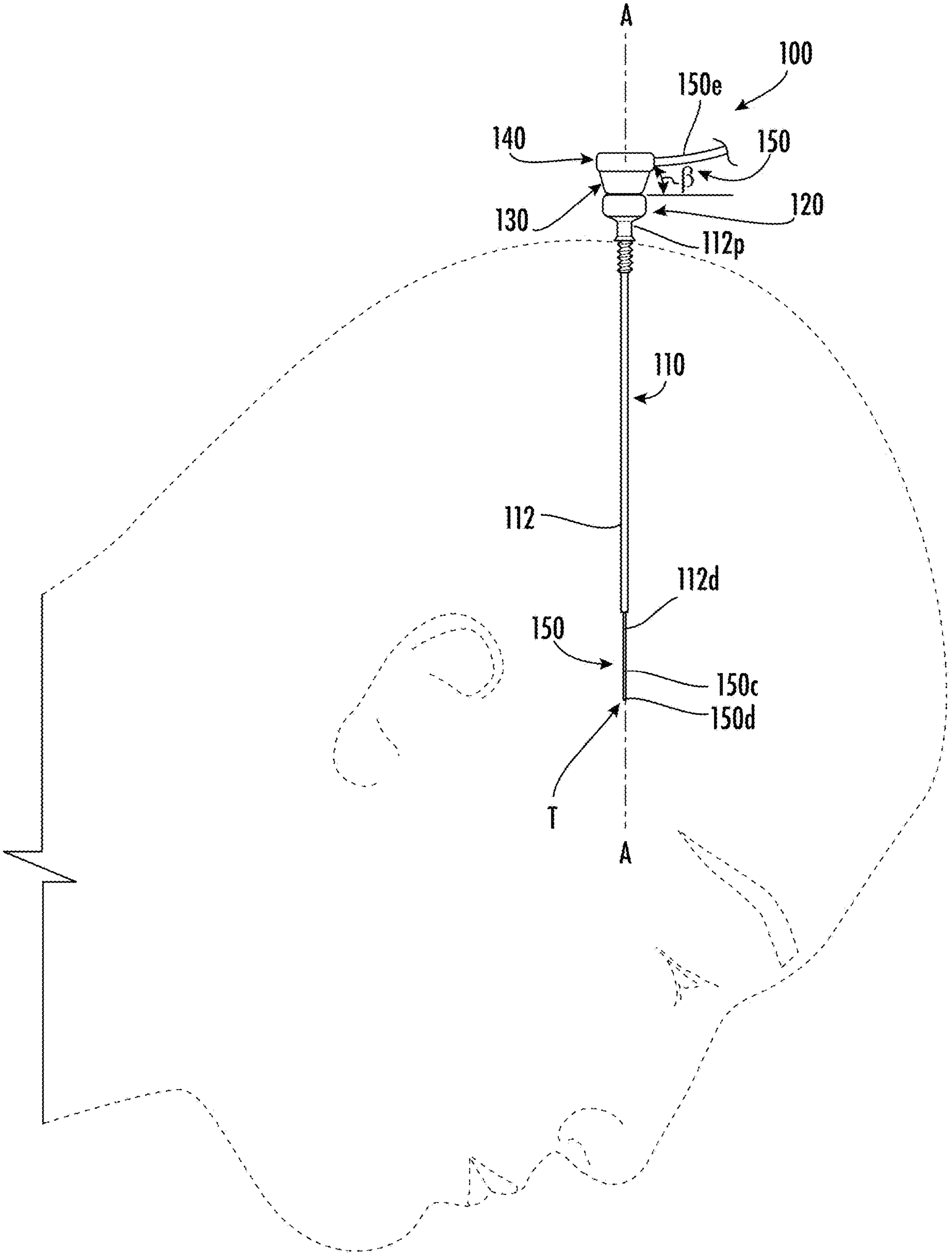
FIG. 4A is a side perspective view of the delivery system shown in FIG. 2 coupled to a therapy device according to embodiments of the present invention.

Referring to FIGS. 4A and 5A, the bolt 120 can have an open longitudinally extending center channel 122 and threads 124 that engage threads 135 of the bolt nut 130. The bolt nut 130 can have a neck 133 with an open center channel 134 that aligns with the lumen 112*l* of the sheath 112. The open center channel 134 of the bolt nut 130, the open center channel 122 of the bolt 120, and the lumen 112*l* of the guide sheath 112, can each (concurrently) engage a therapy device 150 to direct the therapy device 150 to a desired target T.

Figure 11:
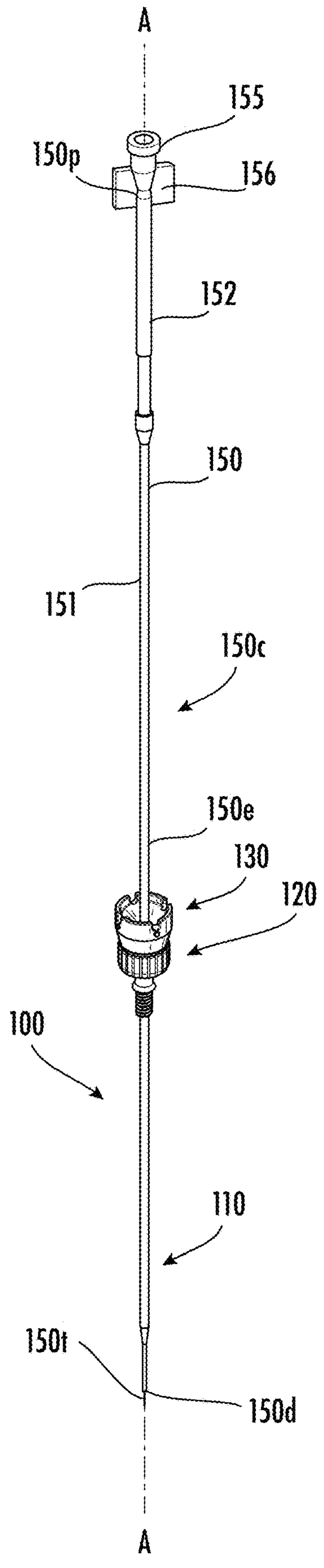
FIG. 11 is a side perspective view of an example therapy device aligned and inserted into and through the bolt nut, bolt and sheath assembly according to embodiments of the present invention.

Referring to FIG. 4A, an external portion 150*e* of the therapy device 150 can exit the bolt nut cap 140 at an angle β of about 60-90 degrees from an axial centerline A-A of the internal portion of the therapy device 150 held by the bolt 120 and/or from a straight orientation of the therapy device before assembly (FIG. 11).

A stylet 210 (FIG. 9D) used to position the guide sheath 112 and the therapy device 150 can each have a length sufficient to serially extend into, typically extend all the way through, the sheath lumen 112*l* of the sheath assembly 110, to position a distal end portion 210*d*, 150*d*, respectively, outside the distal end portion 112*d* of the guide sheath 112 as will be discussed further below.

The therapy device 150 can be flexible. The therapy device 150 can be a catheter 150*c* and may be a flexible ventricular catheter in some embodiments. The therapy device 150 can comprise a thermal probe, such as a cryogenic or laser probe. The therapy device 150 can comprise electrodes such as stimulation electrodes.

Figure 4B:
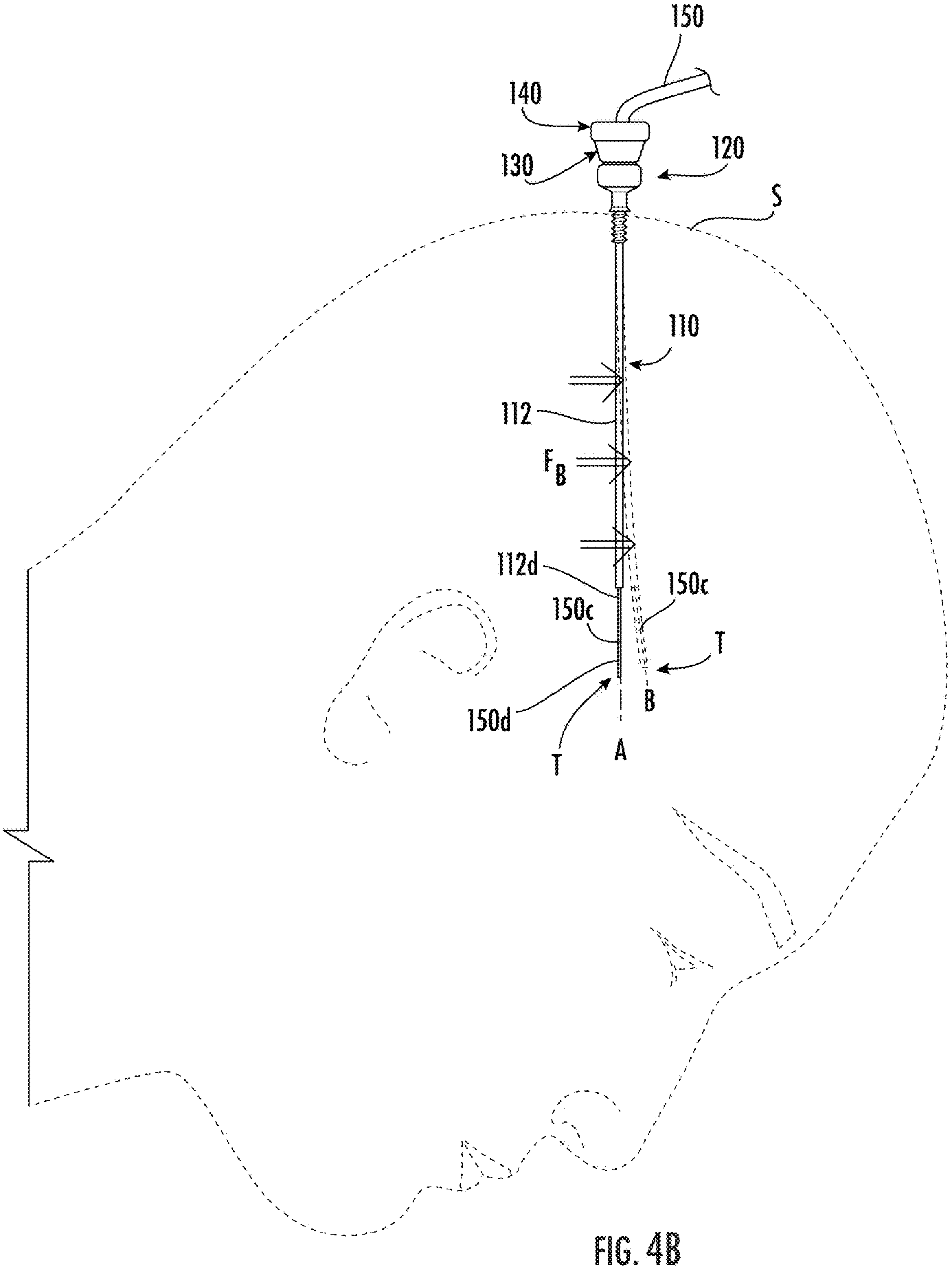
FIG. 4B is a side perspective view of the delivery system shown in FIG. 4A schematically illustrating the flexibility of the system so that the catheter and guide sheath can deflect/shift in response to a deflection load applied by brain tissue during a brain positional shift between positions A and B (relative to the skull/bolt) in the brain while remaining implanted and defining a trajectory to the target according to embodiments of the present invention.

Referring to FIG. 4B, the guide sheath 112 and the therapy device 150, such as a flexible catheter 150*c*, can be sufficiently flexible (alone and in combination) to be able to deflect relative to the skull S and/or bolt 120 in response to a deflection load or force $F_B$ applied by tissue in the brain in response to brain shift that can occur upon patient movement. The deflection load or force $F_B$ can be relatively small, such as in a range of 1 ounce to 3 ounces, in some embodiments. The guide sheath 112 and an implanted/intrabrain portion (e.g., the distal end portion 150*d*) of the therapy device 150 can deflect with the target tissue T from a trajectory $T_A$ to trajectory $T_B$ relative to the skull S to provide a trajectory from the skull S and/or bolt 120 that aligns with the target tissue T. The deflection load $F_B$ can be small as can the positional movement of the guide sheath 112 and therapy device 150 held therein. The deflection can be in any direction responsive to brain shift movement of local tissue and can change over time, e.g., the implanted portions of the guide sheath 112 and therapy device 150 can "float" or "shift" with brain shift as the patient moves. The deflection load $F_B$ can be applied along an entire length or a sub-length of the intrabody/implanted portion of the guide sheath 112 and therapy device 150.

Referring to FIG. 5A, the bolt nut 130 attaches to the bolt 120 and a distal end portion 130*d* of the bolt nut 130 can face and reside adjacent the seal member 115. The bolt nut 130 can clamp and/or push directly or indirectly against the seal member 115 when coupled to the bolt 120 to provide a seal interface thereat to inhibit fluid leakage from the patient body.

Figure 6A:
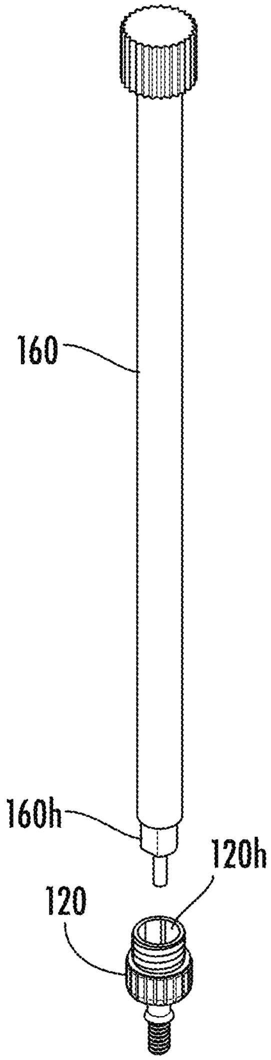
FIG. 6A is a side perspective view of a bolt driver aligned with the bolt shown in FIG. 2.
Figure 6B:
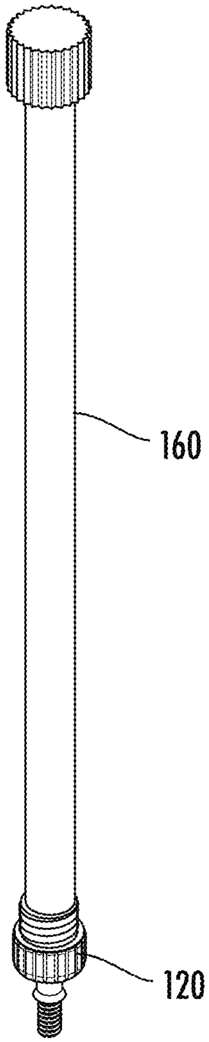
FIG. 6B is a side perspective view of the bolt driver inserted into the bolt to drive the bolt into the skull for the attached position shown in FIG. 2.

An example workflow sequence and associated components for placing the bolt 120, the sheath assembly 110 and other devices will be discussed. Referring to FIGS. 6A and 6B, a bolt driver 160 can be used to drive the bolt 120 into the skull of a patient. The bolt driver 120 includes a bolt engagement member 160*h* that engages corresponding external flats 120*h* (FIG. 14C) on the bolt 120, shown as having a cooperating hex-head configuration.

The bolt driver 160 can have a sufficient length to extend through a tower 1210 (FIG. 21) of a surgical navigation frame assembly 200 that has a frame 200*f* that can reside over a skull and that can define an adjustable/selectable trajectory. Thus, the bolt 120 can be driven into the skull with the bolt driver 160 extending through the tower 160 coupled to the surgical navigation frame assembly.

Figure 7A:
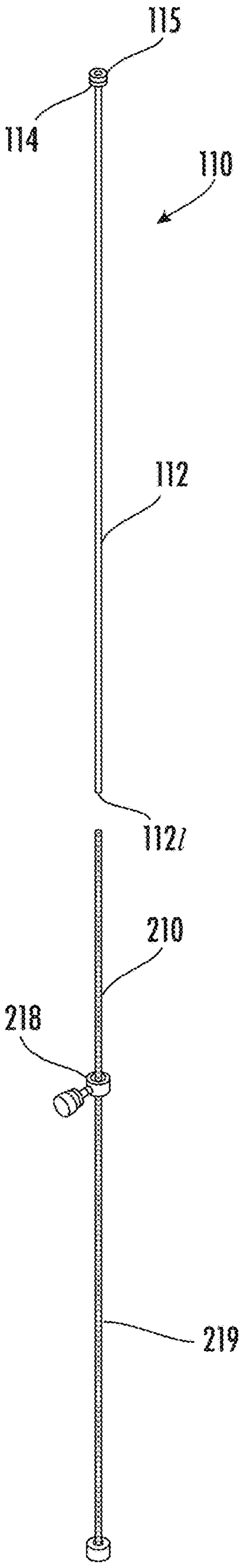
FIG. 7A is a side perspective view of a stylet assembly configured to slidably extend into the lumen of the sheath assembly according to embodiments of the present invention.
Figure 7B:
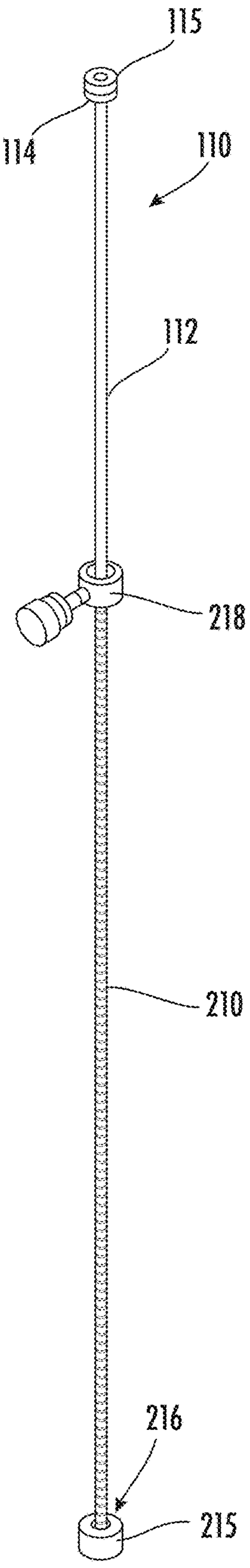
FIG. 7B is a side perspective view of the stylet assembly and sheath assembly shown in FIG. 7A with the stylet assembly inserted into the lumen of the sheath assembly according to embodiments of the present invention.

Referring to FIGS. 7A, 7B, a stylet 210 can be inserted into the sheath assembly 110. The stylet 210 has increased rigidity relative to the guide sheath 112. The stylet 210 can be ceramic in some embodiments. A depth stop 218 can be positioned at a desired location on the stylet 210 to define an adjustable length for a length L of the sheath 112 for the target T of a respective patient (FIG. 2). The stylet 210 can comprise externally visible indicia of length 219 such as graduated markings. The guide sheath 112 can be visually translucent or transparent to allow a user to see the graduated markings when the stylet 210 is inside the guide sheath 112. The guide sheath 112 can be cut to a desired length while the stylet 210 remains inside at least a portion of the guide sheath 112 to avoid kinking or collapse of the guide sheath 112 as a cutting force is applied thereto such as by a scalpel or other cutting tool.

The desired length can be calculated using a position or location of the bolt 120 when it is coupled to the patient. The desired length can be calculated in a planning image(s) based on a defined position of the bolt 120 and the desired T and trajectory path P. For example, once the bolt 120 is coupled to the patient and a trajectory path P determined during an image-guided surgery, the surgical system can obtain one or more images and automatically calculate the length of the guide sheath 112 needed to reach the target site T within a defined precision location, typically within +/−1 mm based on known or calculated tolerances and dimensions of the shoulder 114 of the sheath assembly 110 and its position in the bolt 120 to determine the length L of the guide sheath 112 to reach the target T relative to the cooperating devices.

Figure 8:
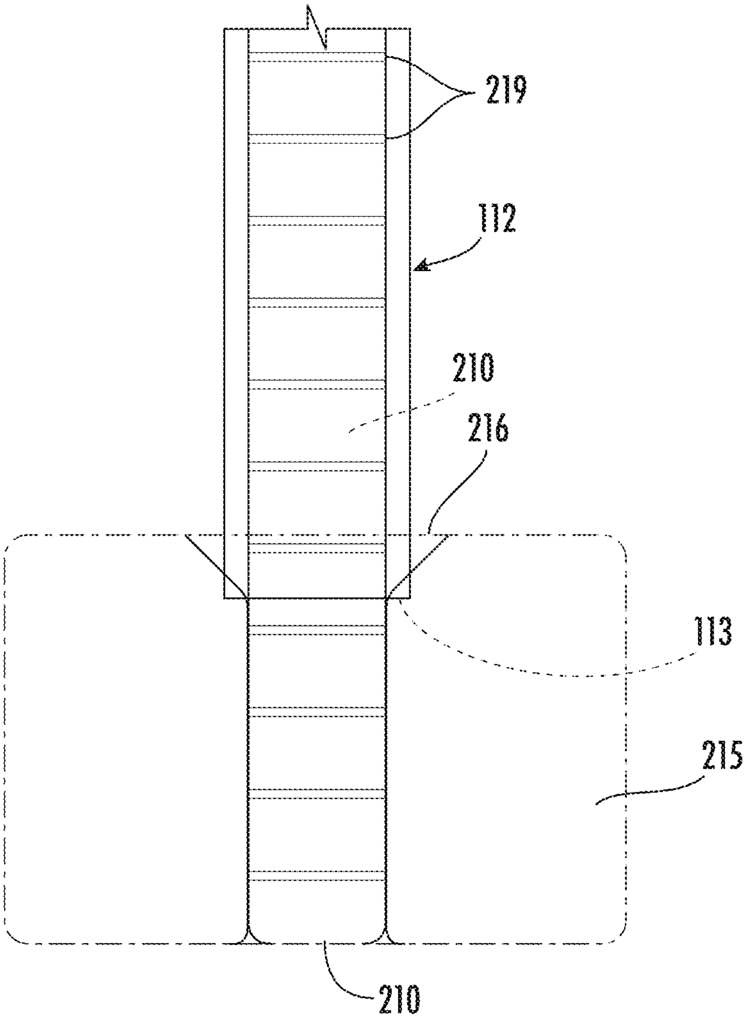
FIG. 8 is an enlarged view of a portion of the stylet assembly shown in FIG. 7A.

Referring to FIGS. 7A, 7B, and 8, the stylet 210 can couple to a stylet shoulder 215 that comprises an open outer facing channel 216. The sheath assembly 110 can be placed onto the stylet 210 until the cut end 113 contacts the channel 216. The cut end 113 of the sheath 112 can be inserted into the channel 216 and the channel 216 and/or the guide sheath 112 can be rotated to profile or otherwise shape the cut end.

The depth stop 218 can be removed from the stylet 210 and the sheath assembly 110 can be removed from the stylet 210 before the profiling.

In other embodiments, a set of sheath assemblies 110*s* (FIG. 20) can be provided with a plurality of sheath assemblies 110, each with a different length of the guide sheath 112.

In yet other embodiments, a custom, patient-procedure specific length of the guide sheath 112 can be made onsite or at an OEM site and provided for a procedure. The length L of the guide sheath 112, and hence placement of the distal end 112*d* of the guide sheath 112, may be important for a precise locational therapy in some uses.

Referring to FIGS. 9A- 9D, the stylet 210 can be inserted through an insertion tool assembly 300 and through the sheath assembly 110. The stylet 210 can be adjusted so that a distal end 210*d* extends out of a distal end 112*d* of the guide sheath 112. The shoulder 114 or the seal member 115 contacts the distal end 302 of the insertion tool assembly 300. A proximal end 210*p* of the stylet 210 can extend out of the insertion tool assembly 300. The stylet 210 can be used in the same orientation or flipped. The shoulder 215, where used, can be removed or positioned above the insertion tool assembly 300.

Figure 9A:
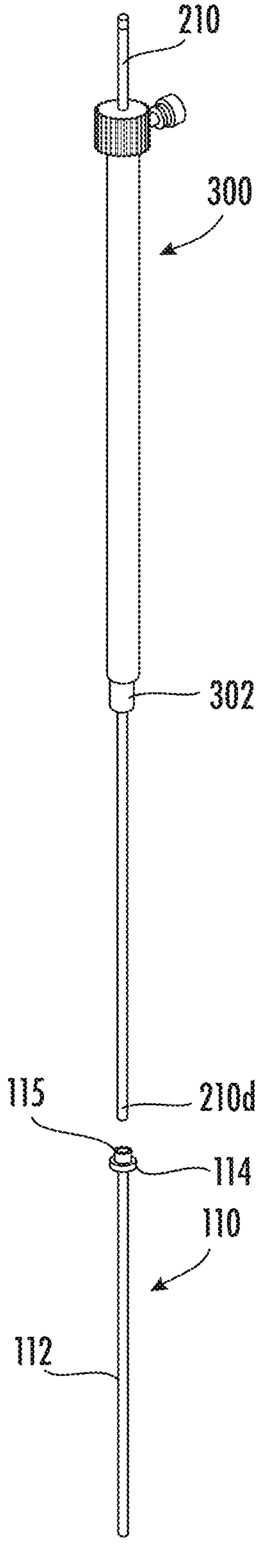
FIGS. 9A-9D are side perspective views of the stylet, a sheath assembly insertion tool showing an example sequence of actions for inserting the sheath assembly into the bolt and into position along a trajectory path in the body according to embodiments of the present invention.
Figure 9B:
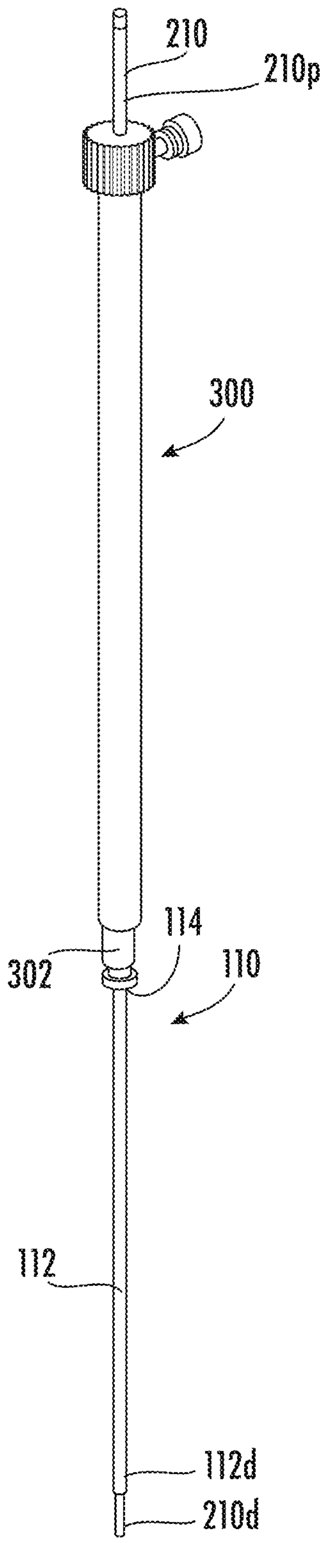
Figure 9C:
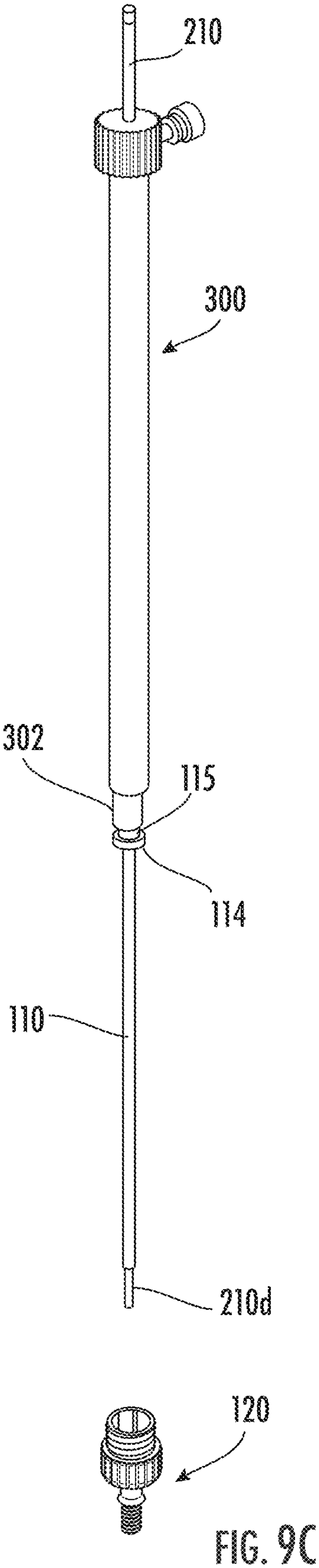
Figure 9D:
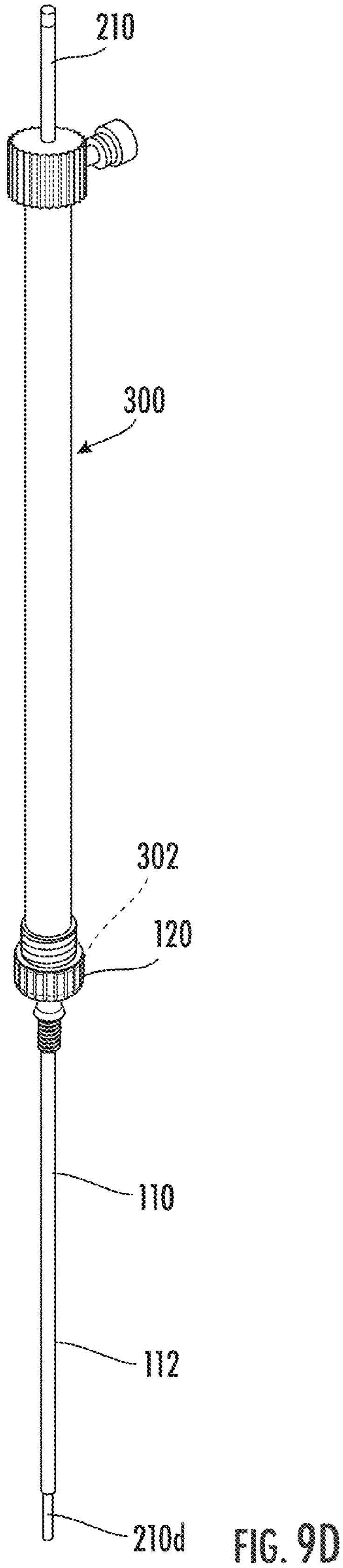
Figure 21:
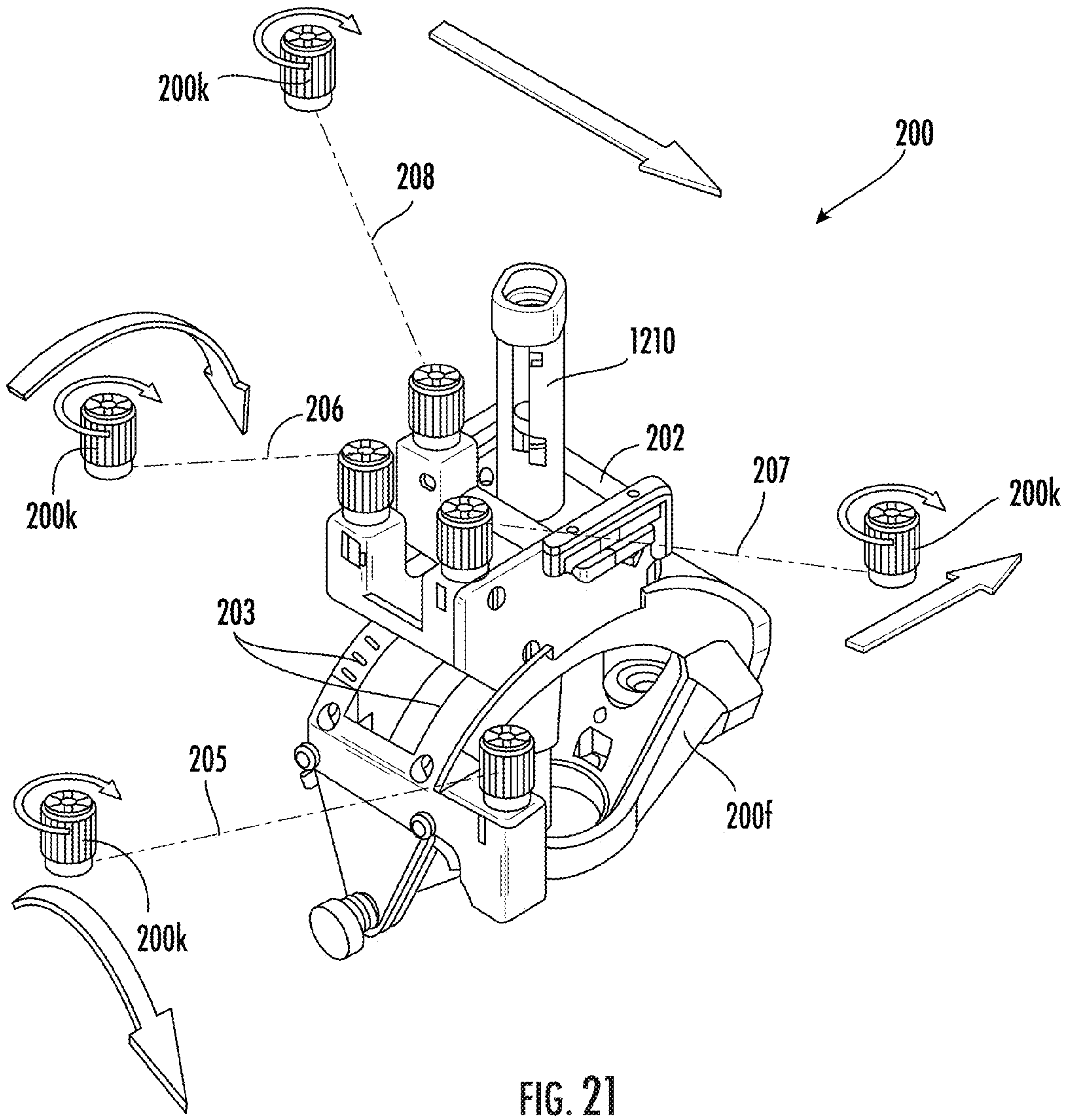
FIG. 21 is an example surgical navigation frame assembly that can be used to place the bolt and guide sheath according to embodiments of the present invention.

The insertion tool assembly 300, coupled to the sheath assembly 110 to form a unit, as shown in FIG. 9C, can be inserted through the tower 1210 of the surgical navigation frame assembly 200 (FIG. 21). As shown in FIG. 9D, a portion of the stylet 210 extends into the bolt 120 and the distal end 302 of the insertion tool assembly 300 enters the bolt 120 to place the sheath assembly 110 into the bolt 120. A distal end 210*d* of the stylet 210 extends out of the guide sheath 112 and provides increased rigidity to allow proper intrabody positioning along the defined trajectory path P (FIG. 2). Once the sheath assembly 110 is in the bolt 120 with the shoulder 114 of the sheath assembly 110 in place in the bolt 120, placing the distal end portion 112*d* of the guide sheath 112 in the proper position, the insertion tool assembly 300 with the cooperating stylet 210 are slidably removed, typically together as a unit. The stylet 210 can be removed from guide sheath 112 (and the tower 1210) separately from the insertion tool assembly 300. In any event, the sheath assembly 110 remains in position with the shoulder 114 held directly or indirectly against the seat 125 inside the bolt 120 after the stylet 210 is slidably removed therefrom.

Figure 10:
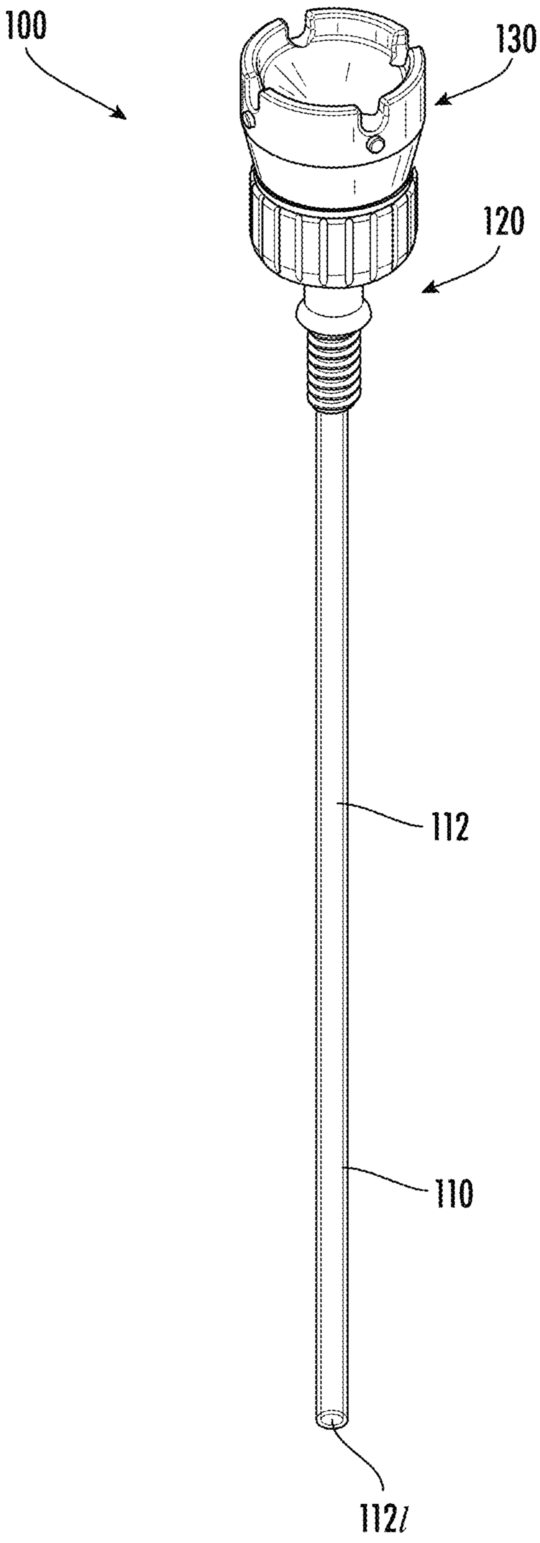
FIG. 10 is an enlarged, side perspective view of the delivery system shown in FIG. 2, shown after placement of the sheath assembly using the stylet and insertion tool shown in FIGS. 9A-9D, according to embodiments of the present invention.

FIG. 10 shows that the bolt nut 130 can then be threaded onto the bolt 120. The sheath assembly 110, the bolt 120 and the bolt nut 130 are coupled together in position to define at least part of a therapy delivery system 100. The bolt nut 130 is not fully tightened at this step.

Referring to FIG. 11, a therapy device 150 is then inserted into the bolt nut 130, the bolt 120 and the lumen 112*l* of the guide sheath 112. A distal end 150*d* of the therapy device 150 typically extends out of the distal end portion 112*d* of the guide sheath 112 to reach the target T. The bolt nut 130 can then be fully tightened/threaded to secure the delivery device 150 to the bolt 120.

The therapy device 150 can be a flexible catheter 150*c*. The therapy device 150 can have an external portion 150*e* that can bend relative to the axial centerline A-A when in a normal insertion orientation (the orientation shown in FIG. 11) as discussed above. The external portion 150*e* can have a first segment 151 with a first outer diameter that merges into a second segment 152 with a second, larger outer diameter. A luer connector 155 can be attached to the second segment 152 at a proximal end portion of the therapy device 150. Outwardly extending wings 156 can be attached adjacent the luer connector 155. The distal end portion 150*d* can have a series of stepped outer diameters of decreasing outer diameter in a direction toward the tip 150*t*. The smallest outer diameter at the tip 150*t* may be defined by a silica tube. The silica tube can extend through the delivery device 150 to the proximal end 150*p*.

Figure 12:
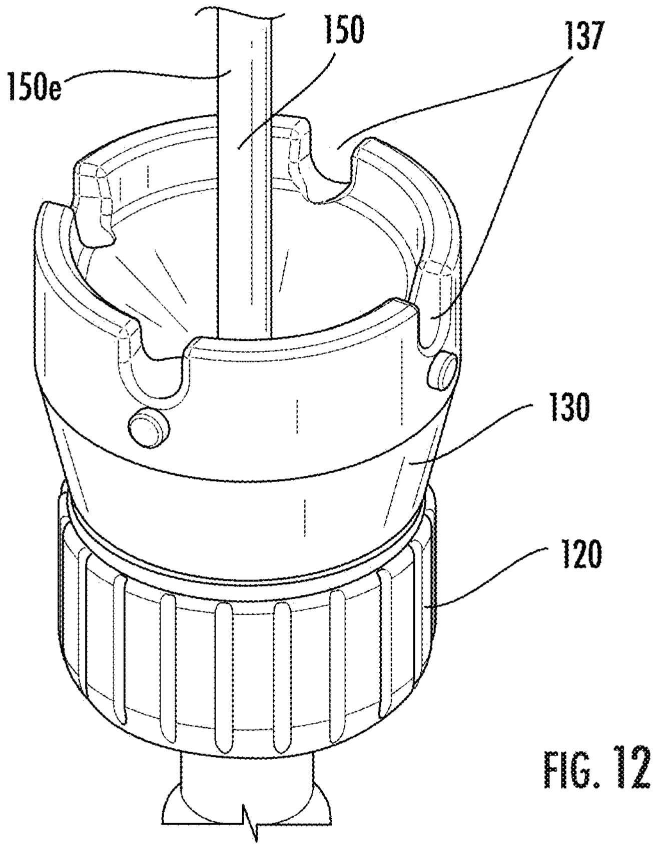
FIG. 12 is a greatly enlarged view of a portion of the bolt and bolt nut shown in FIG. 11.
Figure 13:
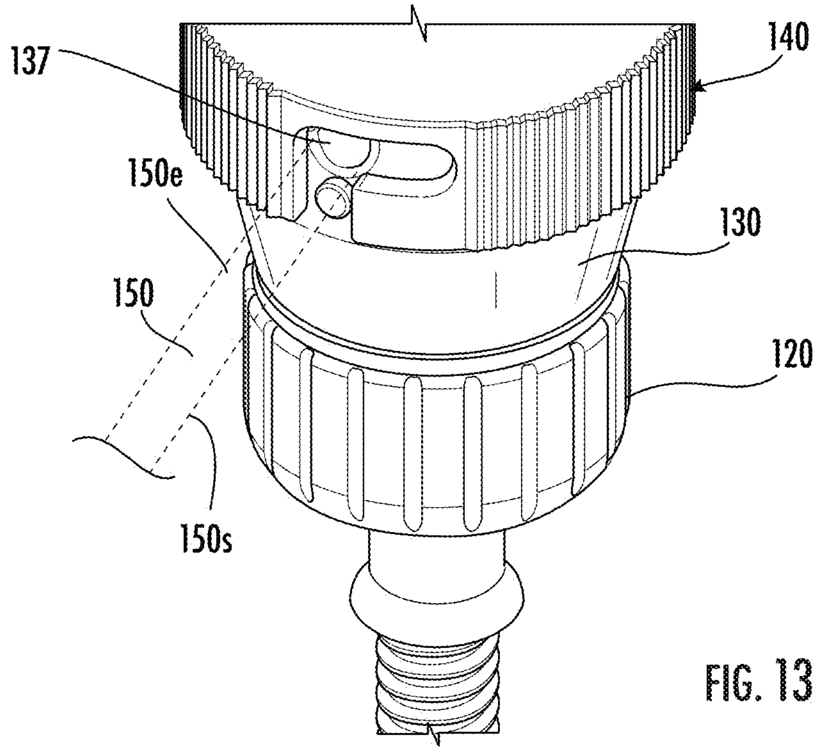
FIG. 13 is a greatly enlarged view of a bolt cap attached to the bolt nut shown in FIGS. 2 and 4A.

Referring to FIGS. 12 and 13, a segment 150*s* of the external portion 150*e* of the delivery device 150 can be bent and routed through one of a plurality of grooves in the bolt nut 130. A cap 140 can be placed onto the bolt nut 130 and twisted to lock the cap 140 to the bolt nut 130 with the segment 150*s* of the device 150 extending out the groove 137.

Referring to FIGS. 4A, 4B, a portion of the flexible catheter 150*c* can remain in the guide sheath 112 in a brain of a patient with the sheath assembly 110 held by the bolt 120 and the bolt nut 130 with another external portion 150*e* residing outside these devices to allow the portion of the flexible catheter in the brain to move with the brain (brain shift) of the patient during treatment thereby allowing or accommodating patient movement in contrast to procedures using rigid catheters.

Figure 14C:
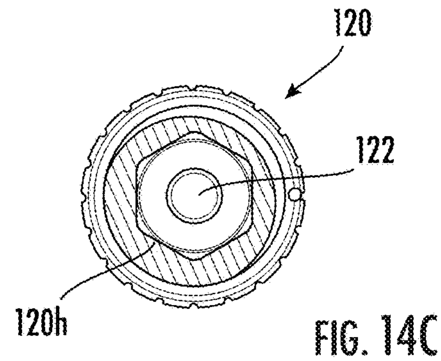
FIG. 14C is a sectional view of the bolt shown in FIG. 14A, taken along line 14C-14C in FIG. 14A.
Figure 14A:
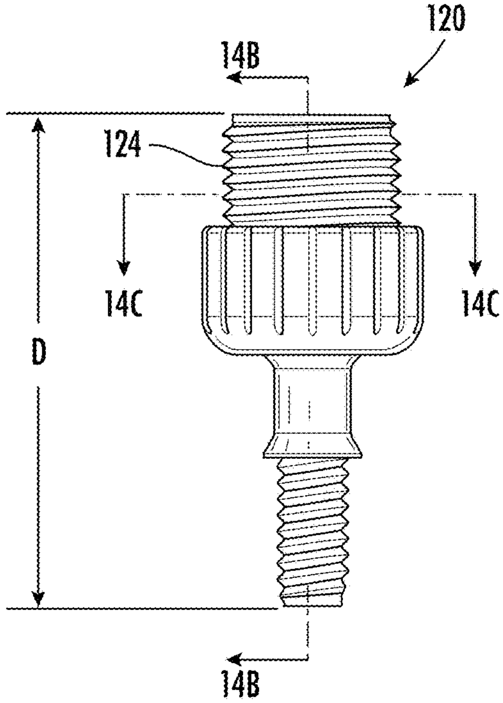
FIG. 14A is a side view of an example bolt.
Figure 14B:
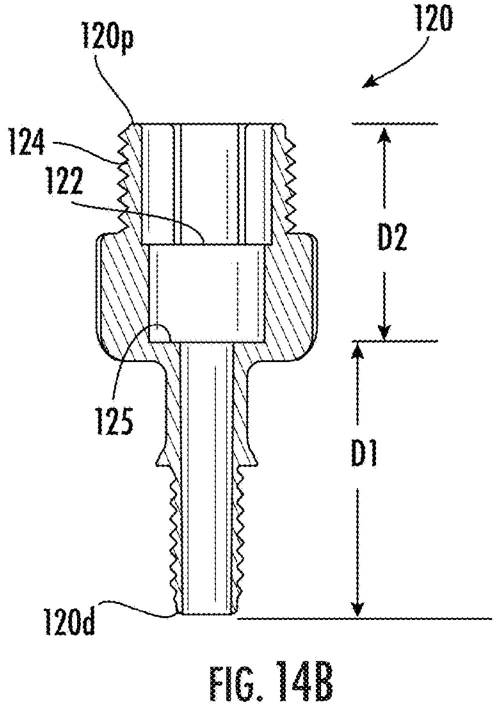
FIG. 14B is a sectional view of the bolt shown in FIG. 14A, taken along line 14B-14B in FIG. 14A.

FIGS. 14A-14C illustrate the bolt 120 with the features discussed above, including the bolt driver engagement features 120*h* (FIG. 14C), the external threads 124 that engage the threads of the bolt nut 130, the open through channel 122 and the seat 125.

FIGS. 14A and 14B illustrate that the bolt 120 can have an overall length "D" that is typically in a range of 0.75-1.25 inches such as about 1 inch. The seat 125 can reside a distance D1 above the distal end 120*d* and a distance D2 below a proximal end 120*p:* D1>D2 in some embodiments; D1=D2 in some embodiments; D2>D1 in some embodiments.

Figure 15A:
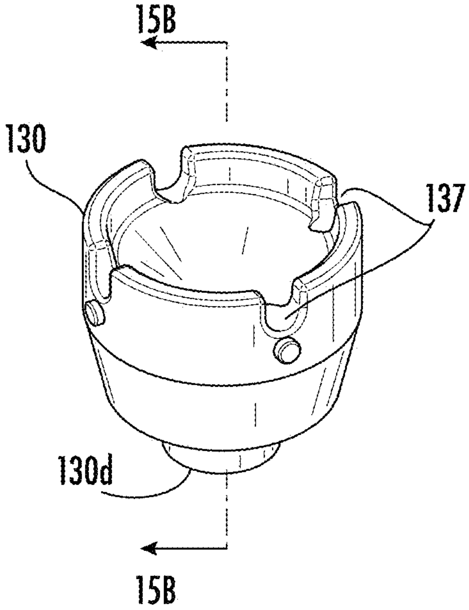
FIG. 15A is a side perspective view of an example bolt nut.
Figure 15B:
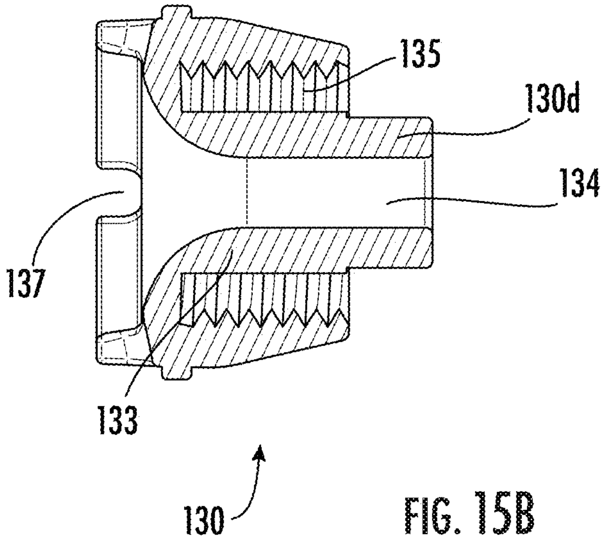
FIG. 15B is a sectional view of the bolt nut shown in FIG. 15A, taken along line 15B-15B in FIG. 15A.

FIGS. 15A and 15B illustrate the bolt nut 130 with features discussed above, including the neck 133, the distal end 130*d,* the through channel 134 and the grooves 137.

Figure 16:
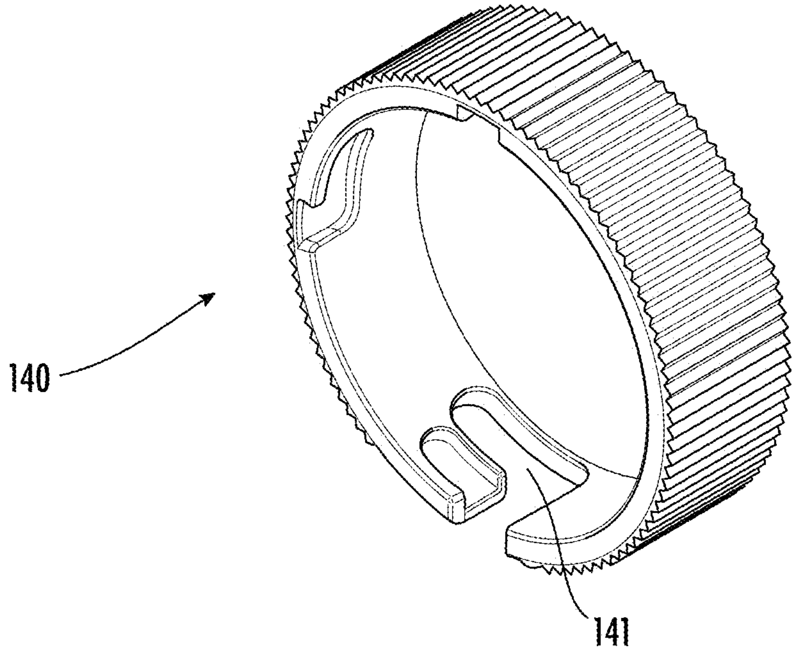
FIG. 16 is a bottom perspective view of an example bolt cap.

FIG. 16 illustrates an example bolt cap 140 with a single circumferentially extending slot 141 that can be rotated to align with a single groove 137 of the bolt nut 130.

Figure 17C:
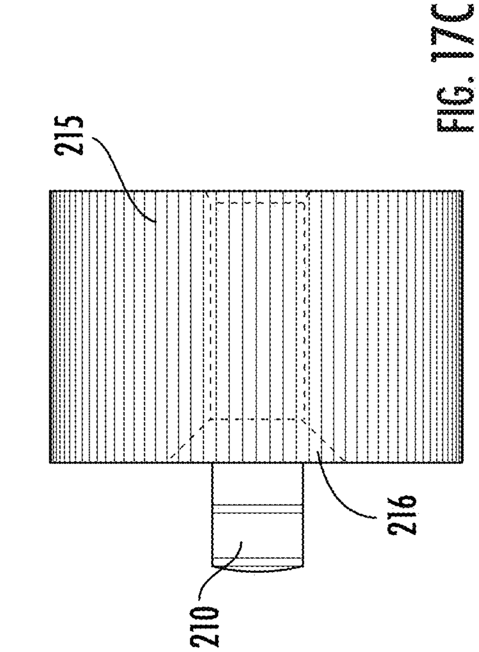
FIG. 17C is an enlarged side view of the end cap shoulder shown in FIG. 17A according to embodiments of the present invention.
Figure 17A:
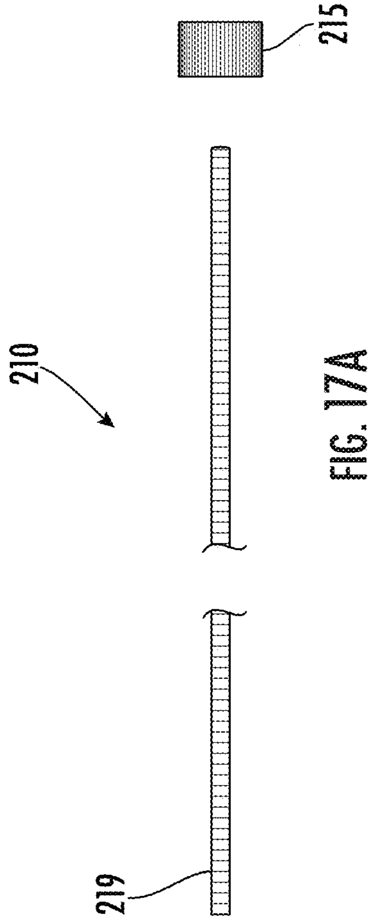
FIG. 17A is a side view of an example stylet according to embodiments of the present invention.
Figure 17B:
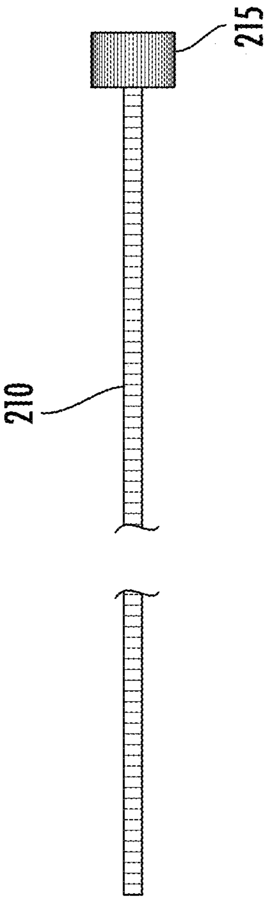
FIG. 17B is an assembled view of the stylet shown in FIG. 17A.

FIGS. 17A-17C illustrate an example stylet 210 and shoulder 215 discussed above, with measurement indicia 219, optionally markings in 1 mm increments.

Figure 18:
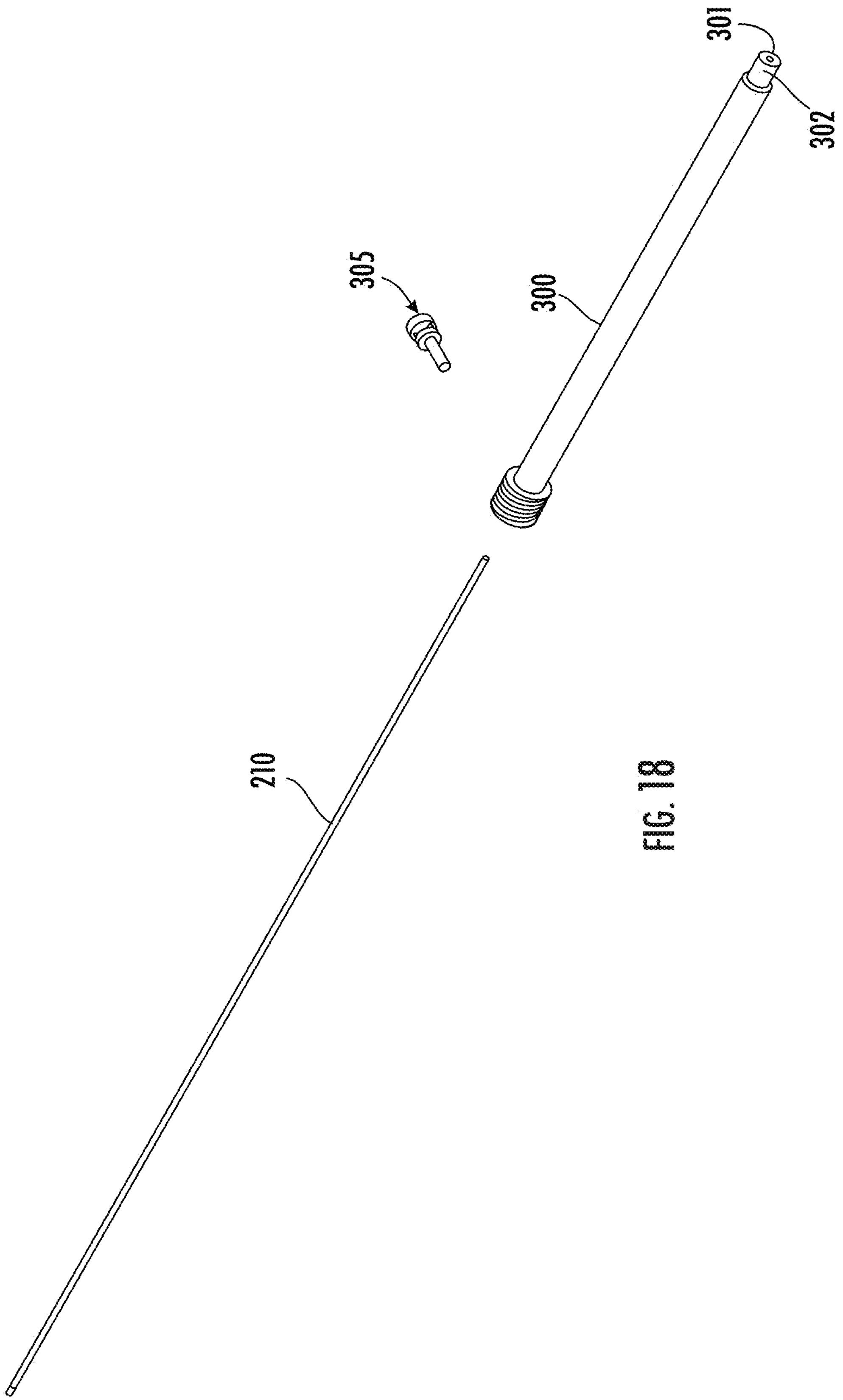
FIG. 18 is an exploded view of the stylet and the insertion tool assembly shown in FIG. 9A according to embodiments of the present invention.

FIG. 18 illustrates the stylet 210 aligned with the insertion tool assembly 300. The insertion tool assembly 300 has an axially extending through channel 301 that slidably receives the stylet 210. The insertion tool assembly 300 includes the distal end 302 that engages the sheath assembly 110 as discussed above. A thumb screw 305 can be used to hold/lock the stylet 210 in a desired position to provide a defined exposed length from the distal end portion 112*d* of the guide sheath 112.

Figure 19:
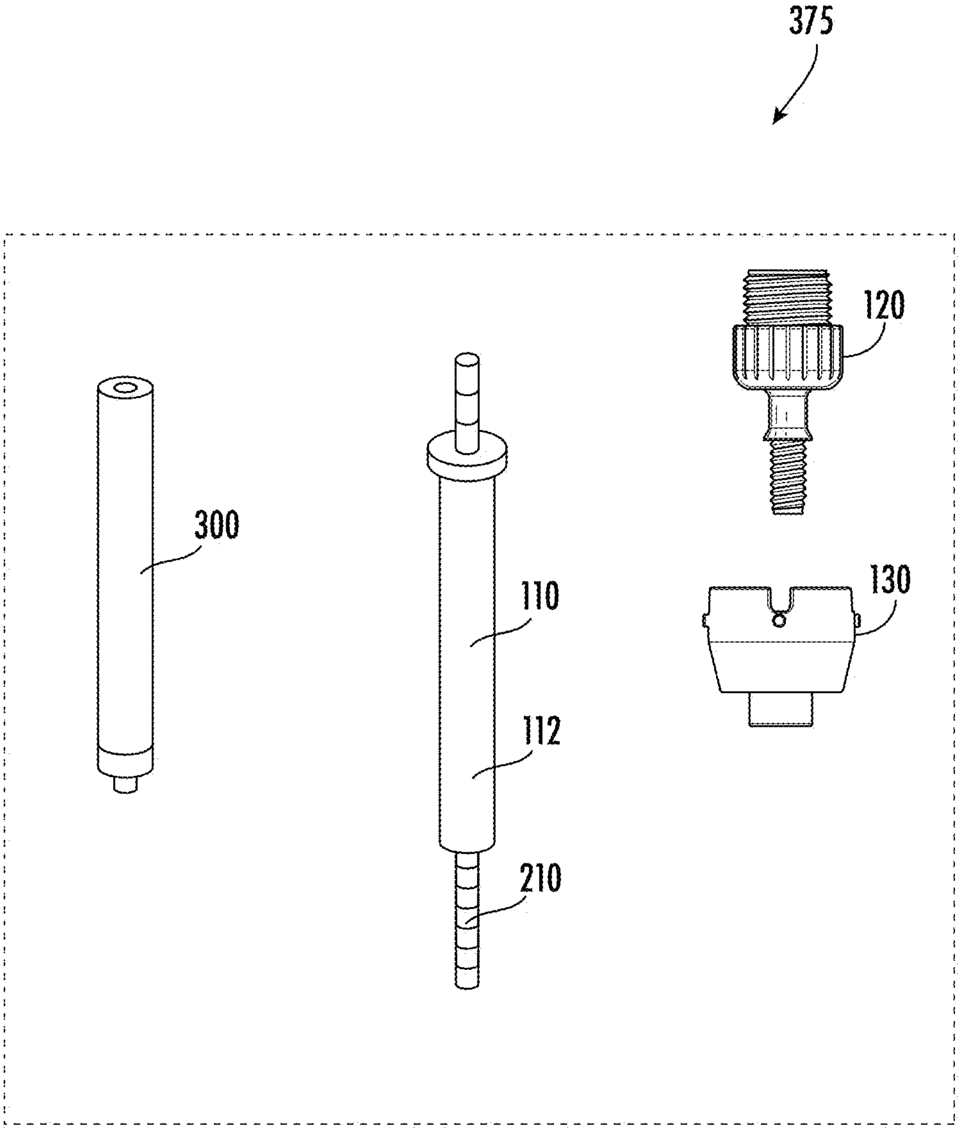
FIG. 19 is a schematic illustration of an example kit of medical parts for a medical procedure according to embodiments of the present invention.

FIG. 19 illustrates an example kit 375 of components for a surgical procedure. The kit 375 can include the insertion tool assembly 300, the sheath assembly 110, the bolt 120 and the bolt nut 130. The stylet 210 can be provided in the sheath assembly 110 to keep the lumen 112*l* open for support during packaging/shipment/prior to use.

Figure 20:
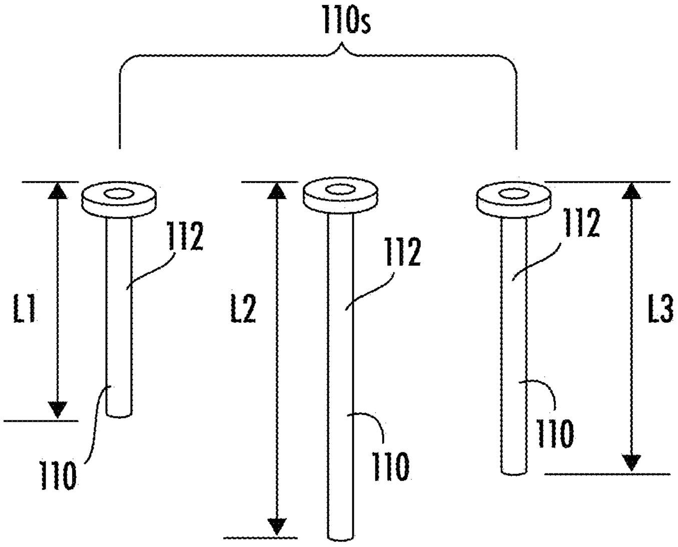
FIG. 20 is a schematic illustration of a set of sheath assemblies with guide sheaths of different lengths according to embodiments of the present invention.

FIG. 20 illustrates that a set 110*s* of sheath assemblies 110 can be provided for a procedure so that a user can select a sheath assembly 110 having a desired length L, e.g., $L_1$, $L_2$, $L_3$. The set 110*s* can be provided with a sufficient number of different lengths for a particular use/patient. The set 110*s* may be provided with respective sheaths 112 in mm and/or cm increments of different lengths over a range or sub-range of lengths from 1 cm to 12 cm.

All components of the kit 375 and/or the therapy system 100 can be made of MRI compatible materials, typically all made of polymeric materials. The term "MRI compatible materials" means that the materials are non-ferromagnetic and do not magnetically interact with the magnetic field of the magnet. The components used in the MR Scanner room are non-metallic and do not generate heat due to RF coupling during scanning.

In some embodiments, the components of the kit 375 that are inserted into the body, i.e., brain, during the medical procedure can be configured to be clearly visible as in images generated from an MRI scan, which allows a clinician such as a surgeon to verify that the guide sheath 112, stylet 210 and/or catheter 150 are placed in a desired position in or at a target intrabody region prior to a therapy such as a fluid transfer.

FIG. 21 illustrates an example surgical navigation frame assembly 200 (also interchangeably referred to as a "trajectory guide") with directional actuators 205, 206, 207, 208 with adjustment knobs 200*k*, an X-Y table 202, arcuate arms 203 and a tower 1210. For additional discussion of examples of suitable surgical navigation frame assemblies see U.S. U.S. Pat. No. 8,374,677, and co-pending U.S. patent application Ser. No. 15/934,165, the contents of which are hereby incorporated by reference as if recited in full herein. However, it is noted that other trajectory guide configurations may be used and embodiments of the invention are not limited by the examples herein.

Embodiments of the present invention may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object-oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 22:
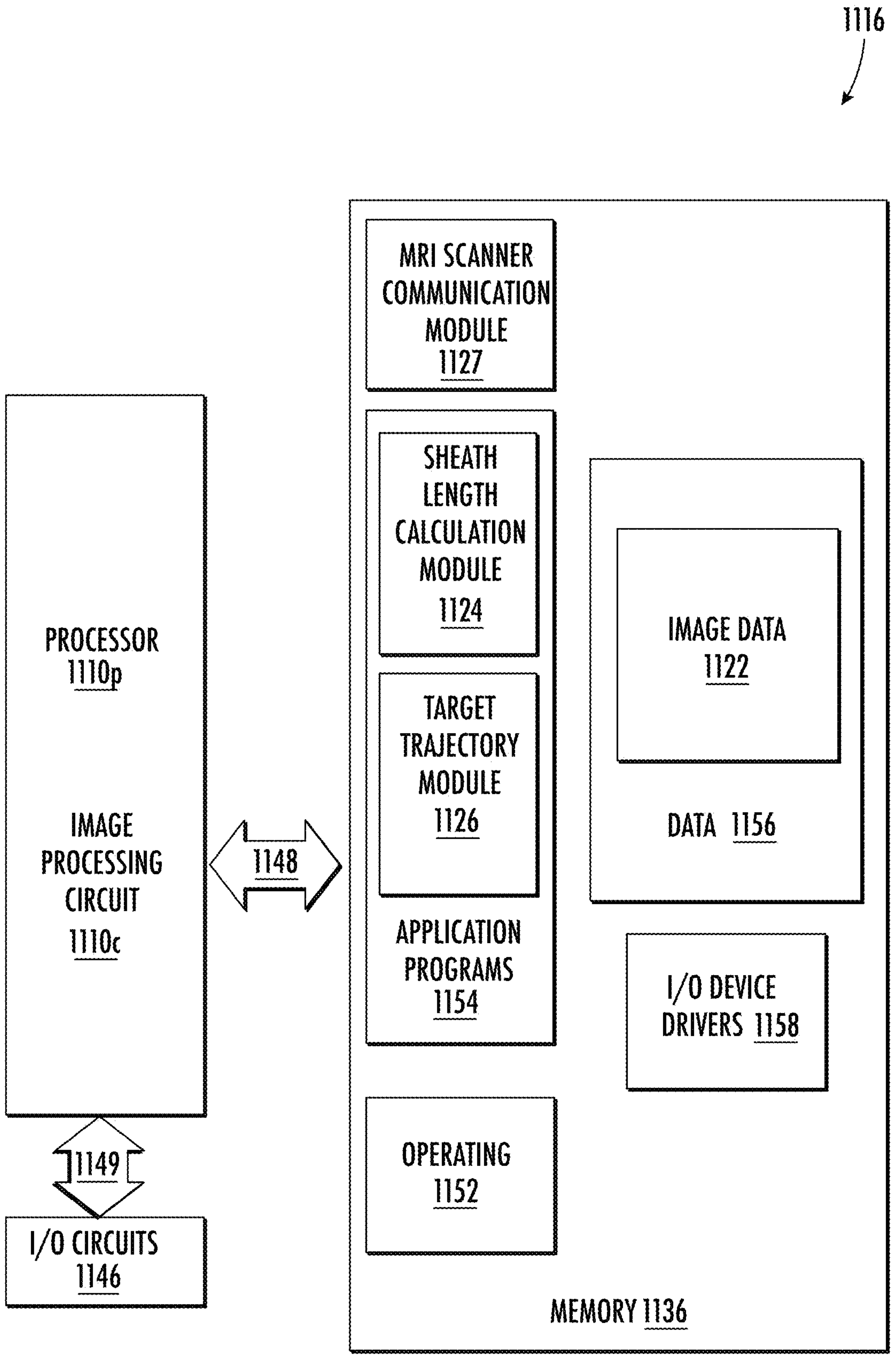
FIG. 22 is a block diagram of a data processing system according to embodiments of the present invention.

As illustrated in FIG. 22, embodiments of the invention may be configured as a data processing system 1116, which can include a (one or more) processors 1110*p*, a memory 1136 and input/output circuits 1146. The one or more processors 1110*p* can be part of the image processing circuit 1110*c*. The data processing system may be incorporated in, for example, one or more of a personal computer, database, workstation, server, router or the like. The system 1116 can reside on one machine or be distributed over a plurality of machines. The processor 1110*p* communicates with the memory 1136 via an address/data bus 1148 and communicates with the input/output circuits 1146 via an address/data bus 1149. The input/output circuits 1146 can be used to transfer information between the memory (memory and/or storage media) 1136 and another computer system or a network using, for example, an Internet protocol (IP) connection. These components may be conventional components such as those used in many conventional data processing systems, which may be configured to operate as described herein.

In particular, the processor 1110*p* can be commercially available or custom microprocessor, microcontroller, digital signal processor or the like. The memory 1136 may include any memory devices and/or storage media containing the software and data used to implement the functionality circuits or modules used in accordance with embodiments of the present invention. The memory 1136 can include, but is not limited to, the following types of devices: ROM, PROM, EPROM, EEPROM, flash memory, SRAM, DRAM and magnetic disk. In some embodiments of the present invention, the memory 1136 may be a content addressable memory (CAM).

As further illustrated in FIG. 22, the memory (and/or storage media) 1136 may include several categories of software and data used in the data processing system: an operating system 1152; application programs 1154; input/output device drivers 1158; and data 1156 including image data 1122. As will be appreciated by those of skill in the art, the operating system 1152 may be any operating system suitable for use with a data processing system, such as LABVIEW®, IBM®, OS/2®, AIX® or zOS® operating systems or Microsoft® Windows®95, Windows98, Windows2000 or WindowsXP operating systems, Unix or Linux™M, IBM, OS/2, AIX and zOS are trademarks of International Business Machines Corporation in the United States, other countries, or both while Linux is a trademark of Linus Torvalds in the United States, other countries, or both and LABVIEW is a registered trademark of National Instruments Corporation. Microsoft and Windows are trademarks of Microsoft Corporation in the United States, other countries, or both.

The input/output device drivers 1158 typically include software routines accessed through the operating system 1152 by the application programs 1154 to communicate with devices such as the input/output circuits 1146 and certain memory 1136 components. The application programs 1154 are illustrative of the programs that implement the various features of the circuits and modules according to some embodiments of the present invention. Finally, the data 1156 represents the static and dynamic data used by the application programs 1154 the operating system 1152 the input/output device drivers 1158 and other software programs that may reside in the memory 1136.

The data 1156 may include MRI image data sets with metadata correlated to respective patients and/or image data for visualizations that can be provided in near real time/real time during a medical procedure, in some embodiments. As further illustrated in FIG. 22, according to some embodiments of the present invention, the application programs 1154 include a sheath length calculation module 1124. The application programs can also include a target trajectory module 1126 and an MRI scanner communication module 1127. The application programs 1154 may be located in a local server (or processor), local client, and/or database or a remote server (or processor), remote client and/or database, or combinations of local and remote databases and/or servers and/or clients.

While the present invention is illustrated with reference to the application programs 1154, and modules 1124, 1126 and 1127 in FIG. 22, as will be appreciated by those of skill in the art, other configurations fall within the scope of the present invention. For example, rather than being application programs 1154 these circuits and modules may also be incorporated into the operating system 1152 or other such logical division of the data processing system. Furthermore, while the application programs 1124, 1126 and 1127 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 22 but may be provided by other arrangements and/or divisions of functions between data processing systems. For example, although FIG. 22 is illustrated as having various circuits and modules, one or more of these circuits or modules may be combined or separated without departing from the scope of the present invention.

Embodiments of the present invention use the surgical support system 100 with an automated or semi-automated surgical navigation system comprising defined workflows and DICOM communication with an MR Scanner. See, e.g., U.S. Pat. No. 10,105,485, the contents of which are hereby incorporated by reference as if recited in full herein.

Figure 23:
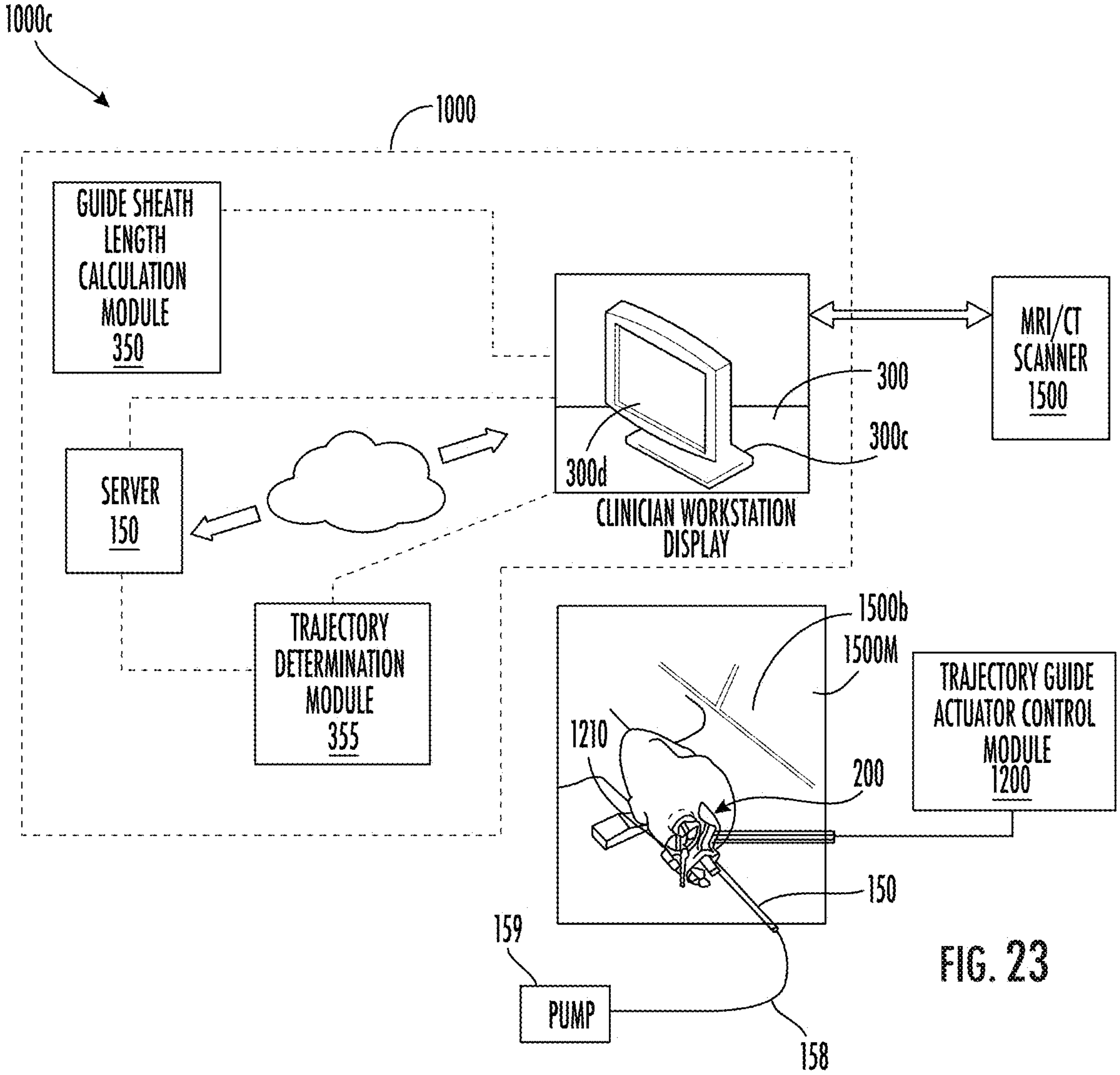
FIG. 23 is a schematic illustration of an image-guided medical system according to embodiments of the present invention.

FIG. 23 illustrates an MRI-guided interventional system 1000 with an MRI scanner 1500, a clinician workstation 300 with at least one image processing circuit 300*c*, at least one display 300*d*, a surgical navigation frame assembly 200 that can provide an MRI compatible trajectory guide and a therapy device 150. Embodiments of the surgical therapy system 100 can be utilized in a bore 1500*b* of a magnet 1500M of an MRI scanner 1500. The system 1000 can include a circuit 1000*c* that also includes a guide sheath length calculation module 350, a trajectory determination module 355 and a server 150. A trajectory guide actuator control module 1200 can also be provided to control actuators of the surgical navigation frame assembly 200.

The therapy device 150 can be coupled flexible tubing 158 that can be coupled to a pump and/or syringe 159. The flexible tubing 158 can have a length that is in a range of about 0.5 feet to about 10 feet long, typically in a range of about 1 foot to about 4 feet long, and more typically in a range of about 2 feet to 3 feet long.

MR visualization may be used to monitor delivery of a therapy with the sheath assembly 110 in position and with the therapy device 150 held by the bolt 120.

Figure 24:
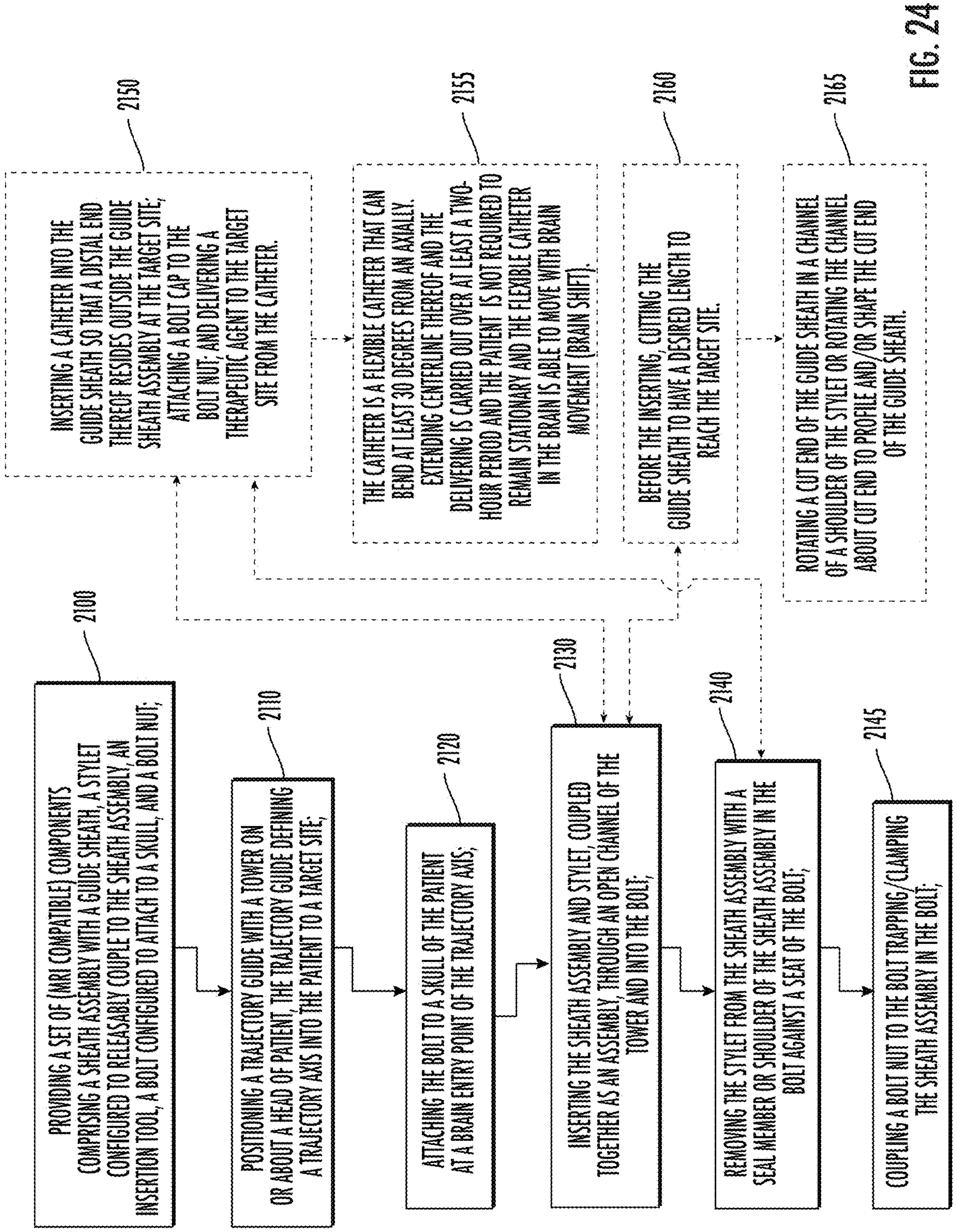
FIG. 24 is a flow chart of example actions that can be carried out according to embodiments of the present invention.

FIG. 24 illustrates an exemplary set of actions for methods that can be used to carry out an image-guided medical procedure, such as position surgical devices for delivering a therapy to a target intrabody site. A set of (optionally MRI compatible) components comprising a sheath assembly with a guide sheath, a stylet configured to releasably couple to the sheath assembly, an insertion tool, a bolt configured to attach to a skull, and a bolt nut (block 2100). A trajectory guide with a tower is positioned on or about a head of patient, the trajectory guide defining a trajectory axis into the patient to a target site (block 2110). The bolt is attached to a skull of the patient at a brain entry point of the trajectory axis (block 2120). The sheath assembly and stylet, coupled together as an assembly, are inserted through an open channel of the tower and into the bolt (block 2130). The stylet is removed from the sheath assembly with a shoulder of the sheath assembly or a seal member in the bolt against a seat of the bolt (block 2140). A bolt nut can then be coupled to the bolt with a proximal end portion thereof facing and adjacent, optionally residing against, the seal member, trapping/clamping the sheath assembly in the bolt (block 2145).

The methods can also include, after the coupling: inserting a catheter into the guide sheath so that a distal end thereof resides outside the guide sheath assembly at the target site; attaching a bolt cap to the bolt nut; and delivering a therapeutic agent to the target site from the catheter (block 2150).

The inserting, removing and coupling can be carried out while the patient is in a magnet of an MR Scanner during an MRI guided surgical procedure.

The methods can further include, before the inserting, cutting the guide sheath to have a desired length to reach the target site (block 2160)

The cutting can be carried out while the stylet is in the guide sheath, optionally with the stylet in a reverse orientation from the inserting orientation.

The methods can further include rotating a cut end of the guide sheath in a channel of a shoulder of the stylet or rotating the shoulder with the cut end of the guide sheath in the channel to profile and/or shape the cut end of the guide sheath (block 2165).

The methods can include routing a segment of the catheter out of a channel defined by cooperating apertures of the bolt cap and bolt nut so that the segment bends at about 90 degrees from an angle of another segment of the catheter that resides distal of the bolt.

The catheter can be a flexible catheter that can bend at least 30 degrees from an axially extending centerline thereof.

The delivering is carried out over at least a two-hour period and the patient is not required to remain stationary and the flexible catheter portion inside the brain is able to deflect/move with brain (shift) movement (block 2155).

The delivering can be carried out, at least in part, after the trajectory guide is taken away or removed.

While the devices have been described herein primarily with reference to MRI-guided procedures, in some embodiments the devices can be used in procedures without MRI guidance, such as with CT-image guided procedures or combinations of the imaging modalities.

The foregoing is illustrative of the present invention and is not to be construed as limiting thereof Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt adjacent the shoulder of the guide sheath; and a bolt nut configured to couple to the bolt, wherein the guide sheath comprises a wall thickness in a range of 0.002 inches to about 0.025 inches, wherein the medical system further comprises a therapy device that extends through the guide sheath so that a distal end portion of the therapy device is distal to the guide sheath, wherein the therapy device and the guide sheath are sufficiently flexible when coupled together to be able to shift in concert in response to brain shift when implanted.

2. The medical system of claim 1, wherein the bolt nut comprises a center projection that resides in the open channel of the bolt and defines a distal portion of the bolt nut that is configured to apply a clamping force against the seal member, wherein the center projection comprises an open center channel, and wherein the bolt nut comprises a proximal portion that has a perimeter with a plurality of circumferentially spaced apart apertures.

3. The medical system of claim 1, wherein the seal member comprises a silicone O-ring.

4. The medical system of claim 1, wherein the guide sheath has a length that is in a range of about 1 cm to about 12 cm, wherein the shoulder resides inside the open channel, and wherein the guide sheath has an open center through lumen that is sized and configured to slidably receive a therapy device.

5. The medical system of claim 4, wherein the guide sheath is configured to be cut to length at a location distal to the shoulder and seal member.

6. The medical system of claim 1, wherein the guide sheath comprises an outer diameter in a range of 2F to 8F.

7. The medical system of claim 1, wherein the guide sheath is formed of medical grade polyethylene, polyimide, PEEK, PEBAX or TEFLON.

8. The medical system of claim 1, wherein the seal member is attached to the shoulder of the sheath assembly.

9. The medical system of claim 1, wherein the bolt nut comprises threads that engage external threads on the bolt, and wherein the bolt nut comprises a distal end that has a laterally extending width and/or radius that matches a laterally extending width and/or outer diameter of the seal member.

10. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt adjacent the shoulder of the guide sheath; and a bolt nut configured to couple to the bolt, wherein the proximal end of the sheath assembly terminates inside the bolt.

11. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt; and a bolt nut configured to couple to the bolt, wherein the sheath assembly is provided as a set of sheath assemblies, each sheath assembly having a guide sheath with a different length to thereby allow a user to select an appropriate sheath assembly with a guide sheath having a desired length to extend to a target site in the patient for a medical procedure.

12. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt adjacent the shoulder of the guide sheath;

a bolt nut configured to couple to the bolt;

a cap that is configured to attach to the bolt nut; and a stylet that has increased rigidity relative to the guide sheath, wherein the stylet is releasably and slidably coupled to the sheath assembly.

13. The medical system of claim 12, wherein the stylet comprises externally visible indicia of length or markings in distance increments.

14. The medical system of claim 12, wherein the stylet comprises an end portion with a shoulder comprising an open, outer facing channel configured to slidably receive the distal end of the guide sheath to thereby profile and/or shape the distal end of the guide sheath.

15. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt;

a bolt nut configured to couple to the bolt;

a stylet that has increased rigidity relative to the guide sheath, and wherein the stylet is releasably and slidably coupled to the sheath assembly; and an insertion tool assembly with an open through channel, configured to attach the sheath assembly to the bolt prior to coupling the bolt nut to the bolt, wherein the stylet releasably extends concurrently through the open through channel of the insertion tool assembly and the lumen of the sheath assembly to provide rigidity during intrabody placement, and wherein, when assembled together, a distal end of the insertion tool assembly abuts the sheath assembly whereby upon insertion into the bolt, the insertion tool assembly places the sheath assembly in the bolt.

16. The medical system of claim 15, further comprising a trajectory guide that is configured to reside over or attach to the patient, the trajectory guide comprising a tower that is moveable to define a trajectory angle, wherein the insertion tool assembly has a length sufficient to extend at least partially through the tower with a proximal end residing outside and more proximal to the tower.

17. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt;

a bolt nut configured to couple to the bolt; and a flexible catheter configured with a portion that slidably extends through the sheath assembly, wherein the flexible catheter has axially opposed proximal and distal ends and a length sufficient to position the distal end internal to the patient outside the distal end of the guide sheath, wherein the flexible catheter has sufficient flexibility to be able to bend at an angle of 45-90 degrees without breaking and wherein the flexible catheter comprises a luer connector on the proximal end.

18. The medical system of claim 17, wherein the flexible catheter comprises an external segment that is configured to reside outside the patient comprising a first segment with a first outer diameter that merges into a second segment with a second, greater outer diameter, that is coupled to the luer connector at the proximal end, wherein the flexible catheter comprises a third segment that is configured to reside inside the patient, wherein the third segment merges into at least one stepped outer diameter segment at a distal end portion thereof that resides outside the guide sheath.

19. The medical system of claim 18, wherein the first segment is configured to be routed through a groove in the bolt and a bolt cap at an angle that is about 90 degrees from an axially extending centerline of the guide sheath and a portion of the flexible catheter held distal to the bolt.

20. A medical system, comprising:

a sheath assembly comprising a guide sheath with a proximal end and an opposing distal end and with a lumen extending therethrough, wherein the proximal end comprises a shoulder that extends radially outward from the lumen;

a bolt configured to threadably engage a skull of a patient, wherein the bolt comprises an open channel that extends axially therethrough, and wherein the guide sheath is configured to reside in the open channel of the bolt with the distal end residing distally of the bolt;

a seal member inside the bolt adjacent the shoulder of the guide sheath; and a bolt nut configured to couple to the bolt, wherein the open channel of the bolt defines a seat for the shoulder of the sheath assembly, and wherein the bolt nut comprises a distal end that resides in the open channel of the bolt and cooperates with the bolt to clamp against the seal member to inhibit fluid leakage from the patient distal to the seal member.

21. An image-guided surgical system comprising:

a surgical navigation trajectory guide comprising a tower that is moveable to define a trajectory path angle;

a sheath assembly comprising a guide sheath with a proximal end and an opposing distal end and with an open through lumen extending therethrough, wherein the proximal end comprises a radially outwardly extending shoulder;

a bolt configured to threadably engage a skull of a patient, wherein the bolt comprises an open channel that extends axially therethrough, wherein the guide sheath is configured to reside in the open channel of the bolt with the distal end residing distally of the bolt and with the proximal end terminating inside the bolt;

a bolt nut configured to couple to the bolt;

a stylet releasably insertable through the sheath assembly; and an insertion tool assembly with an open through channel, configured to attach the sheath assembly to the bolt prior to coupling the bolt nut to the bolt, wherein the stylet releasably and concurrently extends through the open through channel of the insertion tool assembly and the lumen of the sheath assembly, wherein, when assembled together, a distal end of the insertion tool assembly abuts the sheath assembly whereby upon insertion into the bolt, the insertion tool assembly places the sheath assembly in the bolt with the shoulder thereof or a seal member in the bolt against a seat inside the bolt, and wherein the insertion tool assembly has a length sufficient to extend at least partially through the tower with a proximal end residing outside and more proximal to the tower.

22. A method of providing a therapy, comprising:

providing a set of surgical components comprising a sheath assembly with a guide sheath, a stylet configured to releasably couple to the sheath assembly, an insertion tool assembly, a bolt configured to attach to a skull, and a bolt nut;

positioning a trajectory guide with a tower on or about a head of patient, the trajectory guide defining a trajectory axis into the patient to a target site;

attaching the bolt to a skull of the patient at a brain entry point of the trajectory axis;

inserting the sheath assembly, insertion tool assembly and stylet, coupled together as an assembly, through an open channel of the tower and into the bolt;

removing the insertion tool assembly from the tower with or separately from removing the stylet from the sheath assembly; then coupling a bolt nut to the bolt with a distal end portion of the bolt nut facing and adjacent a shoulder of the sheath assembly in the bolt and/or a seal member in the bolt.

* * * * *